US008497262B2

(12) United States Patent
Kaplan et al.

(10) Patent No.: US 8,497,262 B2
(45) Date of Patent: Jul. 30, 2013

(54) THERAPEUTIC PYRAZOLONAPHTHYRIDINE DERIVATIVES

(75) Inventors: Alan P. Kaplan, San Diego, CA (US); Varsha Gupta, Encinitas, CA (US); Jan W. F. Wasley, Guilford, CT (US)

(73) Assignee: Dart NeuroScience (Cayman) Ltd, Grand Cayman (KY)

( * ) Notice: Subject to any disclaimer, the term of this patent is extended or adjusted under 35 U.S.C. 154(b) by 70 days.

(21) Appl. No.: 12/949,619

(22) Filed: Nov. 18, 2010

(65) Prior Publication Data

US 2011/0065692 A1    Mar. 17, 2011

Related U.S. Application Data

(62) Division of application No. 12/135,045, filed on Jun. 6, 2008, now Pat. No. 7,858,614.

(60) Provisional application No. 60/943,000, filed on Jun. 8, 2007.

(51) Int. Cl.
| A61K 31/55 | (2006.01) |
| A61K 31/535 | (2006.01) |
| A61K 31/497 | (2006.01) |
| A61K 31/445 | (2006.01) |

(52) U.S. Cl.
USPC .............. 514/217.04; 514/218; 514/232.2; 514/232.8; 514/253.03; 514/315

(58) Field of Classification Search
USPC ......... 514/217.04, 218, 232.2, 232.8, 253.03, 514/315
See application file for complete search history.

(56) References Cited

U.S. PATENT DOCUMENTS

| 4,552,874 | A | 11/1985 | Mardin et al. |
| 4,690,930 | A | 9/1987 | Takada et al. |
| 4,814,450 | A | 3/1989 | Yokoyama |
| 5,334,595 | A | 8/1994 | Wentland |
| 6,686,373 | B2 | 2/2004 | Kawamura et al. |
| 7,872,002 | B2 * | 1/2011 | Kaplan et al. ............ 514/217.04 |
| 2005/0004159 | A1 | 1/2005 | Hibi et al. |
| 2005/0245563 | A1 | 11/2005 | Boyle et al. |
| 2006/0035919 | A1 | 2/2006 | Matthews et al. |
| 2006/0100229 | A1 | 5/2006 | Hays et al. |
| 2007/0078083 | A1 | 4/2007 | Barlow et al. |

FOREIGN PATENT DOCUMENTS

| EP | 0 214 092 | 8/1986 |
| WO | WO 99/06401 A1 | 2/1999 |

OTHER PUBLICATIONS

Allen et al., "Synthesis of novel 2-Phenyl-2H-pyrazolo[4,3-c]isoquinolin-3-ols: Topological Comparisons with Analogues of 2-Phenyl-2,5-dihydropyrazolo[4,3-c]quinolin-3(3H)-ones at benzodiazepine receptors," J. Med. Chem., 1992, 35(2): 368-374.

Atack et al., "The proconvulsant effects of the $GABA_A$ α5 subtype-selective compound RY-080 may not be α5-mediated", European Journal of Pharmacology, 2006, 548:77-82.
Barnard et al., "International Union of Pharmacology. XV. Subtypes of γ-Aminobutyric $Acid_A$ Receptors: Classification on the Basis of Subunit Structure and Receptor Function" Pharmacol. Rev., 1998, 50(2):291-313.
Carotti et al., "High Affinity Central Benzodiazepine Receptor Ligands. Part 3: Insights Into the Pharmacophore and Pattern Recognition Study of Intrinsic Activities of Pyrazole[4,3-c]quinolin-3-ones," Bioorg. & Med. Chem., 2003, 11(23): 5259-5272.
Fryer et al., "Structure Activity Relationships of 2-Phenylpyrazolo[4,3-c]quinolin-3-ones and their N- and O-Methyl Analogs at Benzodiazepine Receptors," Med. Chem. Res., 1993, 3: 122-130.
Jacobsen et al., "Piperazine imidazo[1,5-a]quinoxaline Ureas as High-Affinity $GABA_A$ Ligands of Dual Functionality", J. Med. Chem., 1999, 42(7): 1123-1144.
Lister et al., "A pharmacokinetic study of CGS-8216, a benzodiazepine receptor ligand, in the rat," Psychopharmacology, 1984, 84: 420-422.
Low et al., "Molecular and Neuronal Substrate for the Selective Attenuation of Anxiety", Science, 2000, 290:131-134.
McKernan et al., "Sedative but not anxiolytic properties of benzodiazepines are mediated by the $GABA_A$ receptor $α_1$ subtype", Nat. Neurosci., 2000, 3:587-592.
Muller, "New trends in benzodiazepine research", Drugs of Today, 1988, 24:649-663.
Rudolph et al., "Benzodiazepine actions mediated by specific γ-aminobutyric $acid_A$ receptor subtypes", Nature, 1999, 401:796-800.
Takada et al., "Thienylpyrazoloquinolines: Potent Agonists and Inverse Agonists to Benzodiazepine Receptors", J. Med. Chem., 1988, 31:1738-1745.
Yokoyama et al., "2-Arylpyrazolo[4,3-c]quinolin-3-ones: Novel agonist, Partial Agonist and Antagonist of Benzodiazepines" J. Med. Chem., 1982, 25:337-339.
International Search Report corresponding to PCT Application No. PCT/US08/66211 mailed Sep. 2, 2008.
International Written Opinion corresponding to PCT Application No. PCT/US08/66211 mailed Sep. 2, 2008.

* cited by examiner

Primary Examiner — James O Wilson
Assistant Examiner — Ebenezer O Sackey
(74) Attorney, Agent, or Firm — Knobbe Martens Olson & Bear, LLP

(57) ABSTRACT

The invention provides a novel chemical series of formula I, as well as methods of use thereof for binding to the benzodiazepine site of the $GABA_A$ receptor and negatively modulating the α5 subtype of $GABA_A$, and use of the compound of formula I for the treatment of $GABA_A$ receptor associated disorders. The general structure of formula I is shown below: (I)

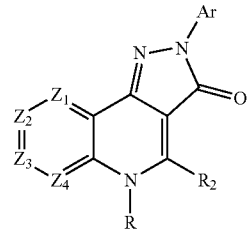

The invention further provides a method of modulation of one or more $GABA_A$ subtypes in an animal comprising administering to the animal an effective amount of a compound of formula (I).

7 Claims, No Drawings

THERAPEUTIC PYRAZOLONAPHTHYRIDINE DERIVATIVES

RELATED APPLICATIONS

This application is a divisional of U.S. patent application Ser. No. 12/135,045, filed Jun. 6, 2008, which claims priority under 35 U.S.C. §119(e) to U.S. Provisional Application No. 60/943,000, filed Jun. 8, 2007; the disclosure of which are incorporated herein by reference in their entireties.

BACKGROUND OF THE INVENTION

1. Field of the Invention

The present invention is related to the use of novel derivatives of pyrazolonaphthyridines as modulators of $GABA_A$ $\alpha 5$ for the intended use of therapy for enhancing cognition.

2. Description of the Related Art

The inhibitory neurotransmitter γ-aminobutyric acid (GABA), serves as a ligand for two distinct classes of receptors, $GABA_A$ and $GABA_B$. The $GABA_A$ class is a ligand-gated ion channel while $GABA_B$ is a canonical seven transmembrane G-protein coupled receptor. The $GABA_A$ receptor is comprised of a number of subunits, including α, β, γ, and δ. Cloning of the individual subunits of the $GABA_A$ receptor has confirmed the existence, so far, of six α subunits, three β subunits, three γ subunits, and one δ subunit. The overall structure of the receptor is a pentamer with a minimum subunit requirement of at least one α subunit, one β subunit, and one γ subunit.

Due to aforementioned diversity of subunits, there are more than 10,000 possible combinations of the subunits that comprise the $GABA_A$ receptor, though not all appear in nature. Specific combinations that have been identified to have biological relevance (and their relative abundance in rat brains, include α1β2γ2 (43%), α2β2/3γ2 (18%), α3βγ2/3 (17%), α2βγ1 (8%), α5β3γ2/3 (4%), α6βγ2 (2%), α6βδ (2%), and α4βδ (3%) (Barnard, E. A., et al. (1998) *Pharmacol. Rev.* 50: 291-313 incorporated herein in its entirety).

There are a number of distinct, small molecule binding sites on the $GABA_A$ receptor that modulate the activity of the receptor including sites for benzodiazepines, steroids, barbiturates, ethanol, and convulsants (e.g. picrotoxin). The GABA binding site is located at the α/β interface. A tremendous amount of pharmaceutical research has been invested in identifying compounds that bind to the benzodiazepine binding site (BZ-site), which is located at the α/γ interface. Binding of GABA is greatly modulated by binding of drugs to the BZ-site, which can cause a number of different pharmacological responses. Drugs such as diazepam and zolpidem, agonists of $GABA_A$ function, have shown historic success as anxiolytic agents (Muller, W. E. (1988) *Drugs of Today* 24: 649-663 incorporated herein in its entirety). More recent work has suggested that the sedative and hypnotic effects of these drugs are primarily due to interaction with the α1-containing receptors, therefore much effort has been focused on finding drugs that have preferential activity towards α2β2γ2 and α3βγ2 over α1βγ2 in order to maintain the anxiolytic activity but reduce the sedative side effects (Rudolph, U. F., et al. (1999) *Nature* 401: 796-800 incorporated herein in its entirety; Löw, K. F., et al. (2000) *Science* 290: 131-134 incorporated herein in its entirety; McKernan, R. M., et al. (2000) *Nat. Neurosci.* 3: 587-592 incorporated herein in its entirety).

The α5-subunit is predominantly found in the hippocampus, a part of the brain that plays a part in memory and spatial navigation. As a result, much research has been focused on identifying links between α5-containing GABA receptor function and cognition. Results from a number of laboratories have indicated that selective inverse agonism of the α5βγ2/3 $GABA_A$ receptor can show marked improvement of memory function in a number of animal models. There have been a growing number of examples of inverse agonists in both the patent and scientific literature (Yokoyama, N., et al. (1982) *J. Med. Chem.* 25: 337-339 incorporated herein in its entirety; Takada, S., et al. (1988) *J. Med. Chem.* 31: 1738-1745 incorporated herein in its entirety; Atack, J. R., et al. (2006) *European Journal of Pharmacology* 548: 77-82 incorporated herein in its entirety). A preferable profile for a cognitive enhancer is one that shows negative modulation at α5, but with less modulation of α1, α2, or α3 to minimize side effects such as convulsion or sedation. As yet, no α5 selective $GABA_A$ negative modulator has been brought to market, and only a limited number have been investigated in human clinical trials.

SUMMARY OF THE INVENTION

Herein described is the composition and use of a new chemical series that is shown to bind to the benzodiazepine site of the $GABA_A$ receptor and negatively modulates the α5 subtype of $GABA_A$. The general structure of formula I is shown below:

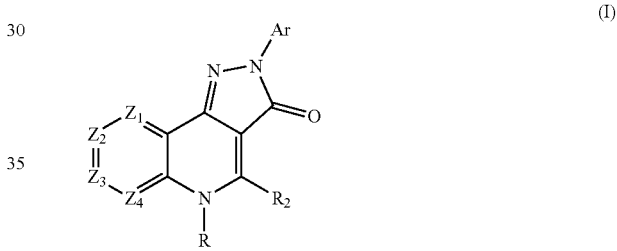

(I)

The compounds of Formula I encompass all possible tautomers of the chemical structures and mixtures thereof.

EMBODIMENTS, ASPECTS AND VARIATIONS OF THE INVENTION

It is recognized in the following structures, when a formula is depicted as a mixture of two tautomeric structures, that the definitions of "R" can be different in the structure on the left than in the structure on the right. For example, in a compound of formula (I), in the structure on the left the definition of "R" can be absent and in the structure on the right the definition of "R" can be hydrogen. Compounds represented by the tautomeric structures can exist in all possible tautomeric forms and mixtures thereof. Additionally, compounds need not exist in both drawn tautomeric forms. A compound that can be represented by either drawn structure, whether in equilibrium or not in equilibrium, falls within the present disclosure.

It is recognized, that two tautomeric forms are drawn for some formulas. For simplicity, in some places (including theclaims), only the tautomeric form on the right is drawn for an indicated formula, this is not to exclude the other tautomeric form. In places where only one tautomeric form is drawn for a formula the other tautomeric form is also contemplated.

One embodiment of the invention provides a compound of formula (I):

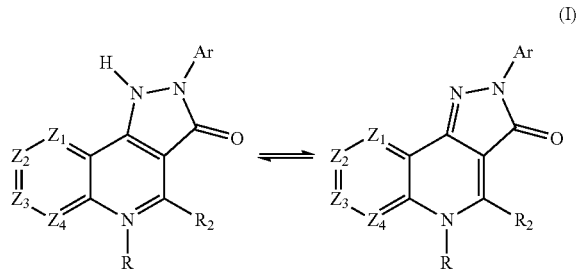

wherein:

R is absent, hydrogen, or oxide;

$Z_1$, $Z_2$, $Z_3$, and $Z_4$ are each independently N, or $C(R_1)$, wherein at least one of $Z_1$, $Z_2$, $Z_3$, or $Z_4$ are N and at least two of $Z_1$, $Z_2$, $Z_3$, or $Z_4$ are $C(R_1)$;

each $R_1$ is independently selected from the group consisting of hydrogen, hydroxy, halo, cyano, $B^1$, —$CONR_aR_b$, —$NR_aR_b$, hydroxy$(C_1-C_6)$alkyl, aryl, heteroaryl, heterocycle, amino$(C_1-C_6)$alkyl, $(C_1-C_6)$alkyl optionally substituted with up to 5 fluoro, and $(C_1-C_6)$alkoxy optionally substituted with up to 5 fluoro, wherein at least one $R_1$ is $B^1$;

$B^1$ is

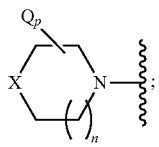

$R_2$ is selected from the group consisting of hydrogen, hydroxy, halo, hydroxy$(C_1-C_6)$alkyl, $(C_1-C_6)$alkyl optionally substituted with up to 5 fluoro, and $(C_1-C_6)$alkoxy optionally substituted with up to 5 fluoro;

each $R_a$ and $R_b$ is independently hydrogen, $(C_1-C_6)$alkyl, aryl, heteroaryl, heterocycle, $(C_1-C_6)$alkylaryl, —$S(O)_z(C_1-C_6)$alkyl, —$S(O)_z$aryl, —$C(O)(C_1-C_6)$alkyl, —$C(O)NR_g(C_1-C_6)$alkyl, —$C(O)NR_g$aryl, —$C(O)O(C_1-C_6)$alkyl, arylOC(O)— or arylC(O)—, or $R_a$ and $R_b$ are taken together with the nitrogen to which they are attached to form a heterocycle group optionally substituted with one or more $R_d$; wherein the heterocycle group optionally include one or more groups selected from O (oxygen), S (sulfur), and $NR_c$;

each $R_c$ is independently hydrogen, $(C_2-C_6)$alkenyl, $(C_2-C_6)$alkynyl, —$C(O)O(C_1-C_6)$alkyl, —$C(O)O$aryl, $(C_1-C_6)$alkoxy$(C_1-C_6)$alkyl, hydroxy$(C_1-C_6)$alkyl, aryl, heteroaryl, heterocycle, arylO$(C_1-C_6)$alkyl, —$C(O)NR_g(C_1-C_6)$alkyl, —$C(O)NR_g$aryl, —$S(O)_z(C_1-C_6)$alkyl, —$S(O)_z$aryl, —$C(O)(C_1-C_6)$alkyl, arylC(O)—, $(C_1-C_6)$alkyl optionally substituted with up to 5 fluoro, or $(C_1-C_6)$alkoxy optionally substituted with up to 5 fluoro;

each $R_d$ is independently hydrogen, halo, oxo, hydroxy, —$C(O)NR_eR_f$, —$NR_eR_f$, hydroxy$(C_1-C_6)$alkyl, aryl, aryl$(C_1-C_6)$alkyl, $(C_1-C_6)$alkyl optionally substituted with up to 5 fluoro, or $(C_1-C_6)$alkoxy optionally substituted with up to 5 fluoro;

each $R_e$ and $R_f$ is independently selected from hydrogen, $(C_1-C_6)$alkyl, aryl, heteroaryl, heterocycle, $(C_1-C_6)$alkylaryl, aryl$(C_1-C_6)$alkyl, —$C(O)(C_1-C_6)$alkyl, —$S(O)_z(C_1-C_6)$alkyl, —$S(O)_zNR_g(C_1-C_6)$alkyl, —$S(O)_z$aryl, —$C(O)NR_g(C_1-C_6)$alkyl, —$C(O)(C_1-C_6)$alkyl, arylC(O)—, arylOC(O)—, or —$C(O)O(C_1-C_6)$alkyl;

$R_g$ is hydrogen, aryl, heteroaryl, heterocycle or $(C_1-C_6)$alkyl optionally substituted with up to 5 fluoro;

Ar is aryl optionally substituted with one or more M or heteroaryl optionally substituted with one or more M;

each Q is independently hydrogen, halo, oxo, hydroxy, —$C(O)NR_aR_b$, —$NR_aR_b$, $(C_1-C_6)$alkyl optionally substituted with up to 5 fluoro, $(C_1-C_6)$alkoxy optionally substituted with up to 5 fluoro, $(C_1-C_6)$alkyl optionally substituted with one or more $R_d$, hydroxy$(C_1-C_6)$alkyl optionally substituted with one or more $R_d$, aryl optionally substituted with one or more $R_d$, or aryl$(C_1-C_6)$alkyl optionally substituted with one or more $R_d$;

each M is independently hydrogen, halo, $CF_3$, $CF_2H$, hydroxy, cyano, nitro, $(C_1-C_6)$alkyl, hydroxy$(C_1-C_6)$alkyl, $(C_1-C_6)$alkoxy, —$NR_aR_b$, aryl, hetero aryl or heterocycle;

each X is independently NL, oxygen, $C(O)_2$, or $S(O)_z$;

each L is independently hydrogen, $(C_2-C_6)$alkenyl, $(C_2-C_6)$alkynyl, —$C(O)O(C_1-C_6)$alkyl, —$C(O)O$aryl, $(C_1-C_6)$alkoxy$(C_1-C_6)$alkyl, hydroxy$(C_1-C_6)$alkyl, aryl, heteroaryl, heterocycle, arylO$(C_1-C_6)$alkyl, —$CONR_eR_f$, —$S(O)_z(C_1-C_6)$alkyl, —$S(O)_z$aryl, —$C(O)(C_1-C_6)$alkyl, arylC(O)—, —$C(O)NR_g(C_1-C_6)$alkyl, $(C_1-C_6)$alkyl optionally substituted with up to 5 fluoro, or $(C_1-C_6)$alkoxy optionally substituted with up to 5 fluoro;

p is an integer selected from 0, 1, 2 and 3;

z is an integer selected from 0, 1 and 2; and n is an integer selected from 0, 1, and 2.

In some embodiments, Ar can be:

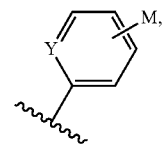

wherein Y is CM or N.

In one embodiment the compound has the formula Ia:

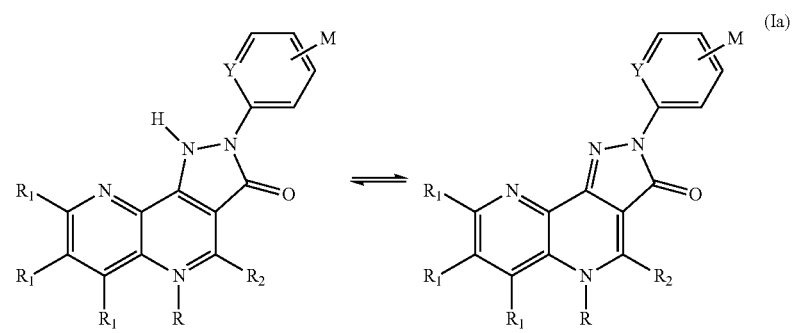

or tautomer thereof, or their pharmaceutically acceptable salts, wherein Y is CM or N. In one embodiment, X can be NL. In another embodiment, X can be oxygen.

In another embodiment the compound has the formula Ib:

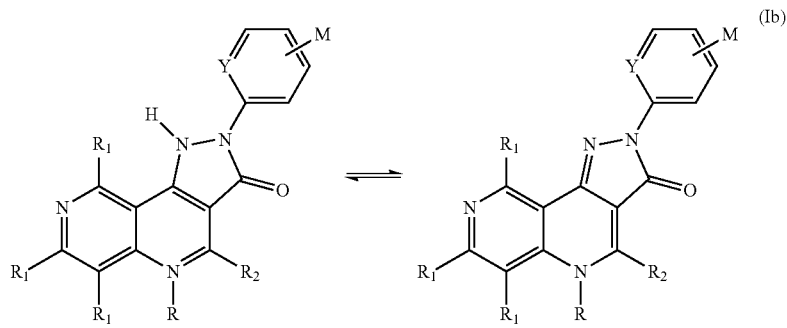

and tautomers thereof, or their pharmaceutically acceptable salts, wherein Y is CM or N. In one embodiment, X can be NL. In another embodiment, X can be oxygen.

In another embodiment the compound has the formula (Ih)

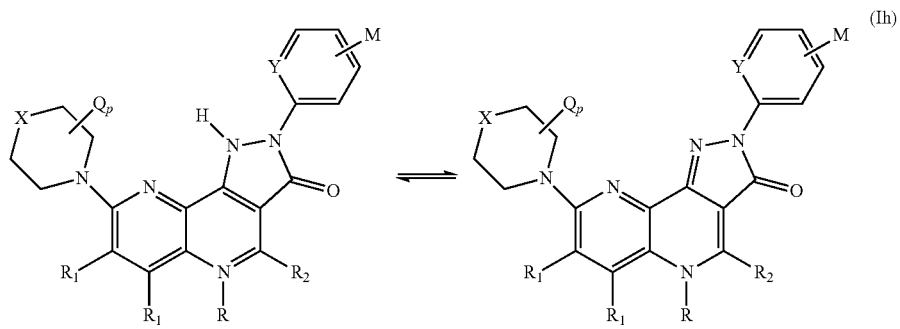

or tautomer thereof, or their pharmaceutically acceptable salts, wherein Y is CM or N.

In another embodiment the compound has the formula (Ii)

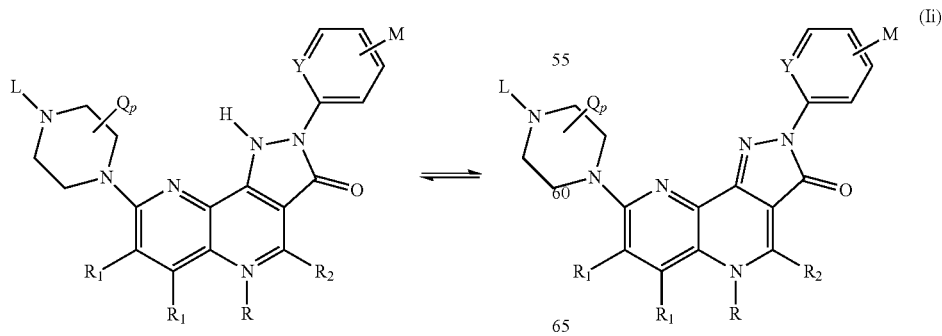

In another embodiment the compound has the formula (Ij)
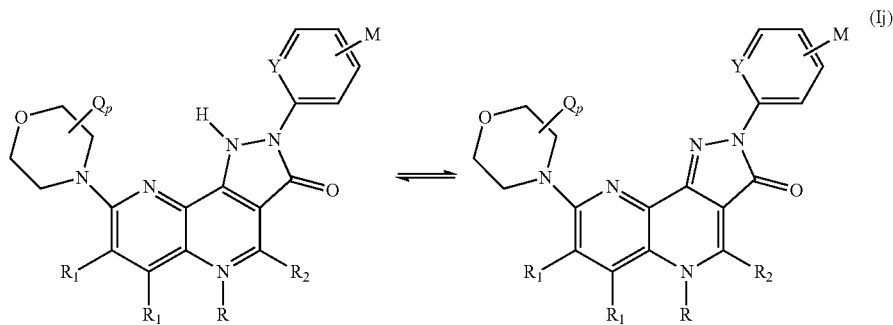
or tautomer thereof, or their pharmaceutically acceptable salts, wherein Y is CM or N.
In another embodiment the compound has the formula (Ik)
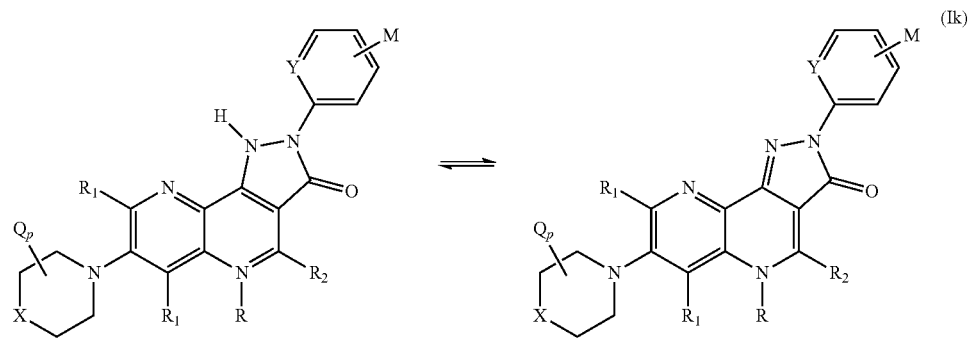
or tautomer thereof, or their pharmaceutically acceptable salts, wherein Y is CM or N.
In another embodiment the compound has the formula (Il)
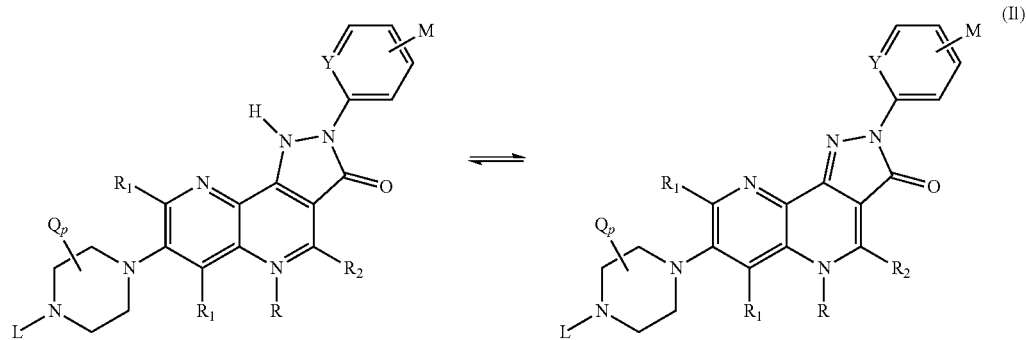

or tautomer thereof, or their pharmaceutically acceptable salts, wherein Y is CM or N.

In another embodiment the compound has the formula (Im)

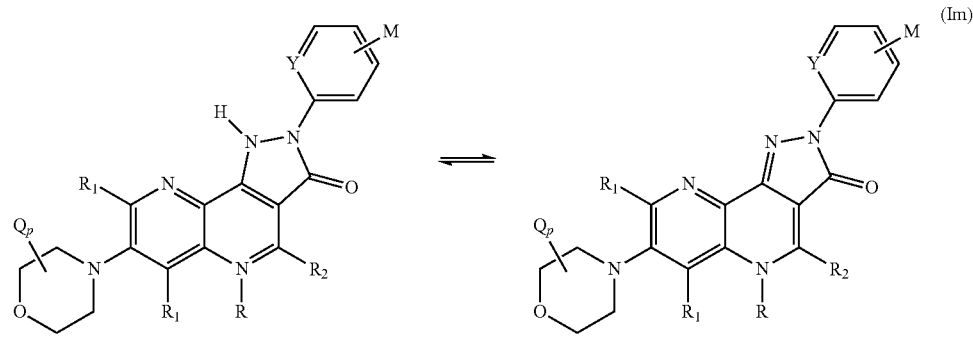

or tautomer thereof, or their pharmaceutically acceptable salts, wherein Y is CM or N.

In another embodiment the compound has the formula (In)

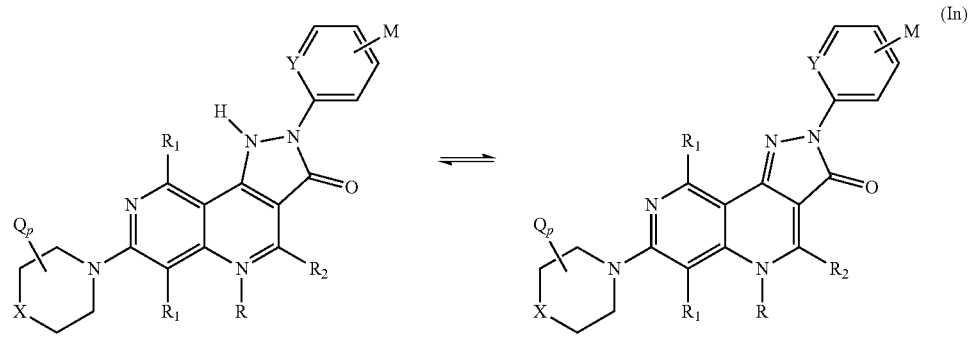

or tautomer thereof, or their pharmaceutically acceptable salts, wherein Y is CM or N.

In another embodiment the compound has the formula (Io)

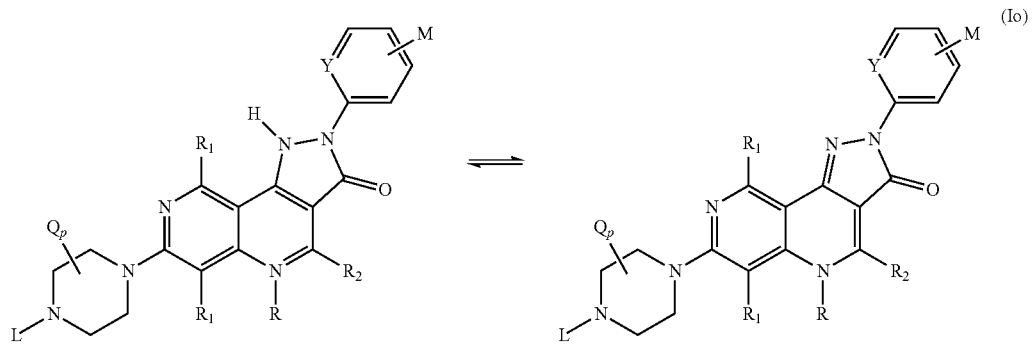

or tautomer thereof, or their pharmaceutically acceptable salts, wherein Y is CM or N.

In another embodiment the compound has the formula (Ip)

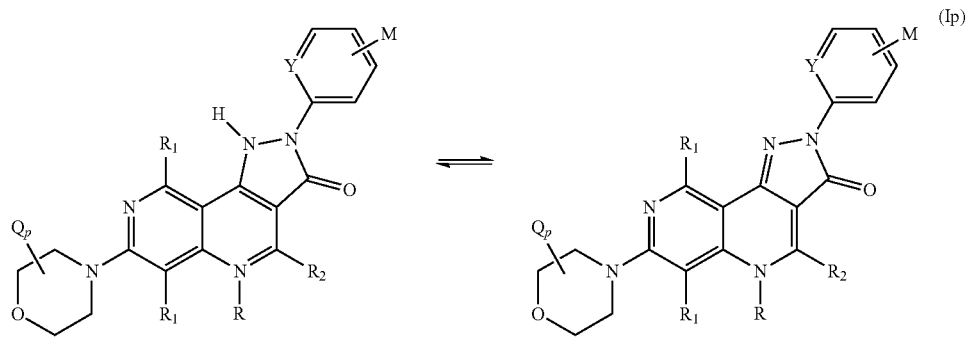

or tautomer thereof, or their pharmaceutically acceptable salts, wherein Y is CM or N.

In another embodiment the compound has the formula (Iq)

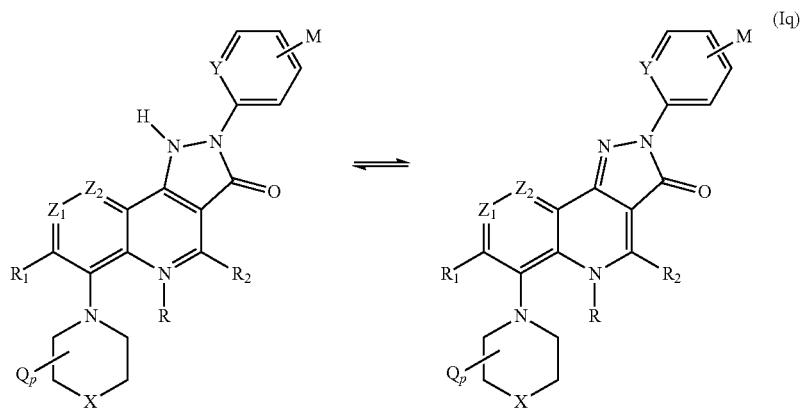

or tautomer thereof, or their pharmaceutically acceptable salts, wherein Y is CM or N.

In another embodiment the compound has the formula (Ir)

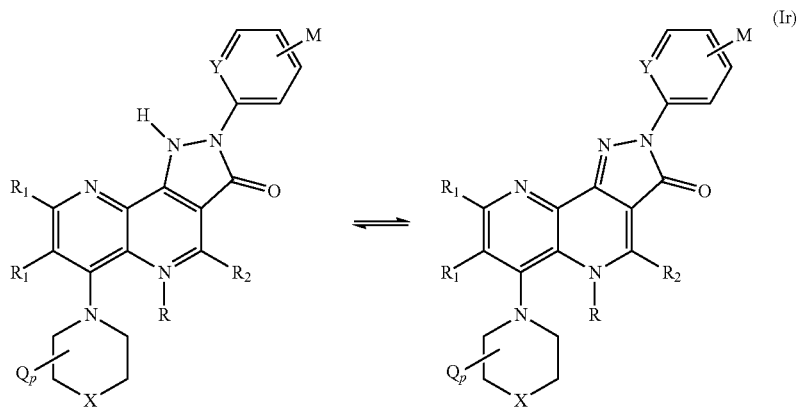

and tautomers thereof, or their pharmaceutically acceptable salts, wherein
Y is CM or N.

In another embodiment the compound has the formula (Is)

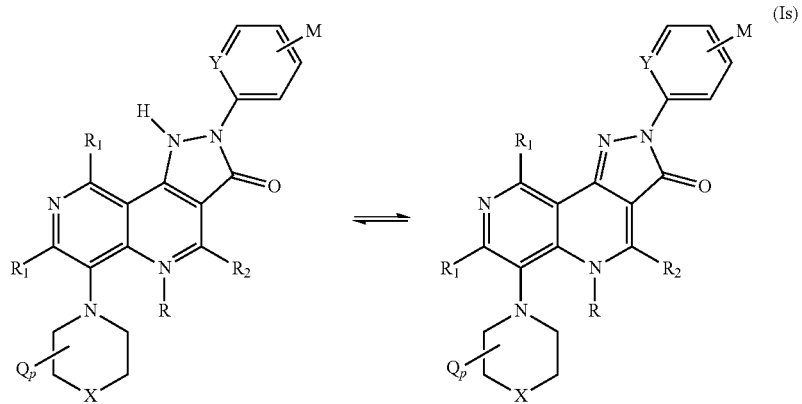

or tautomer thereof, or their pharmaceutically acceptable salts, wherein Y is CM or N.

In another embodiment the compound has the formula (It)

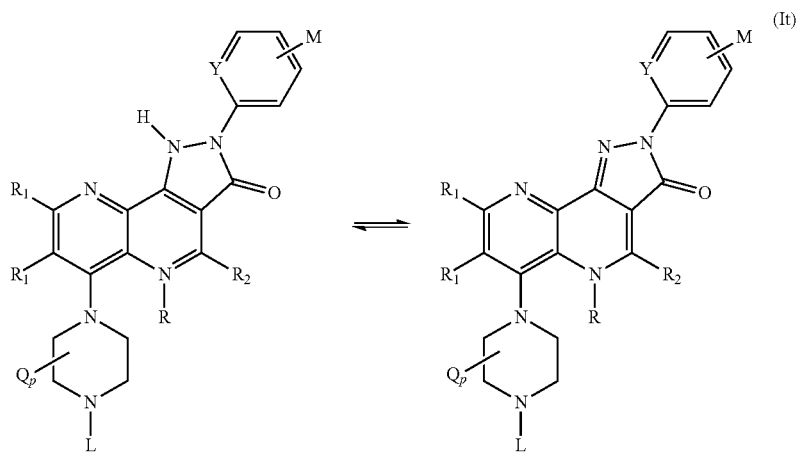

or tautomer thereof, or their pharmaceutically acceptable salts, wherein Y is CM or N.

In another embodiment the compound has the formula (Iu)

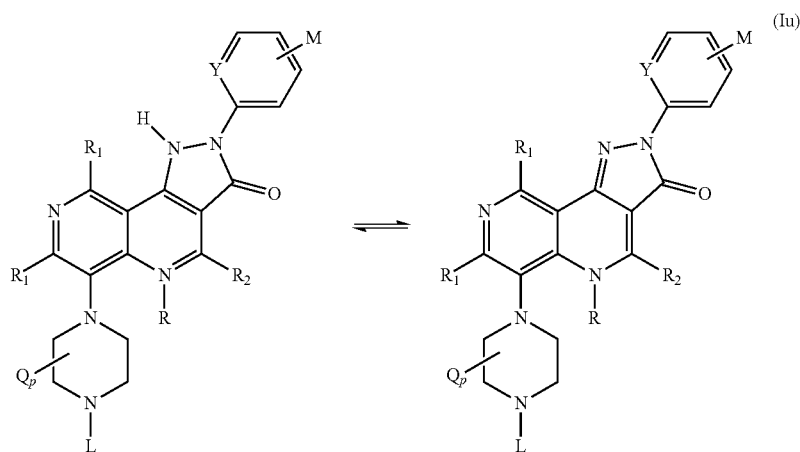

or tautomer thereof, or their pharmaceutically acceptable salts, wherein Y is CM or N.

In another embodiment the compound has the formula (Iv)

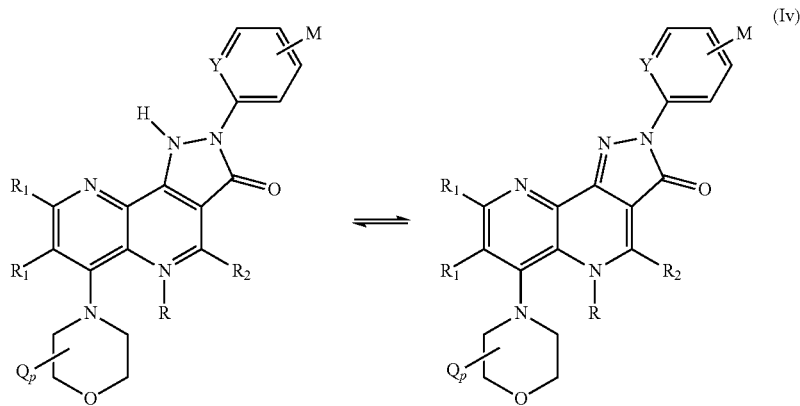

or tautomer thereof, or their pharmaceutically acceptable salts, wherein Y is CM or N.

In another embodiment the compound has the formula (Iw)

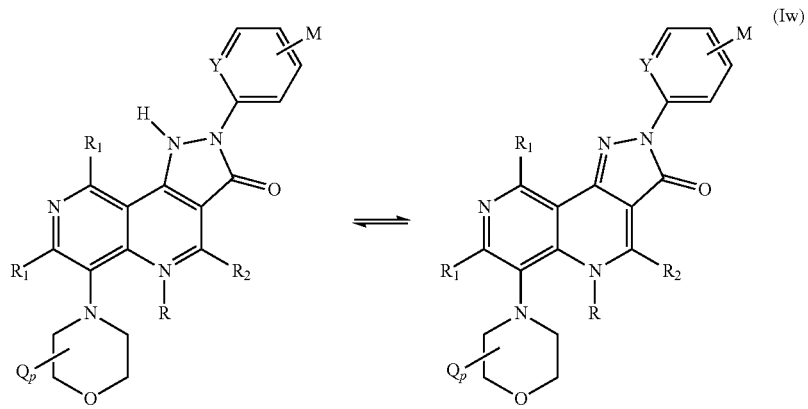

and tautomers thereof, or their pharmaceutically acceptable salts, wherein

Y is CM or N.

In another embodiment the compound is selected from the group consisting of:

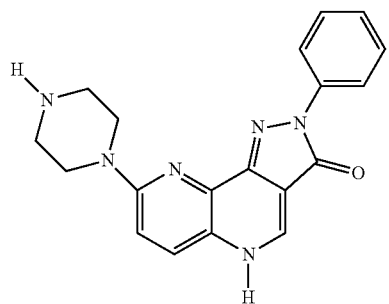

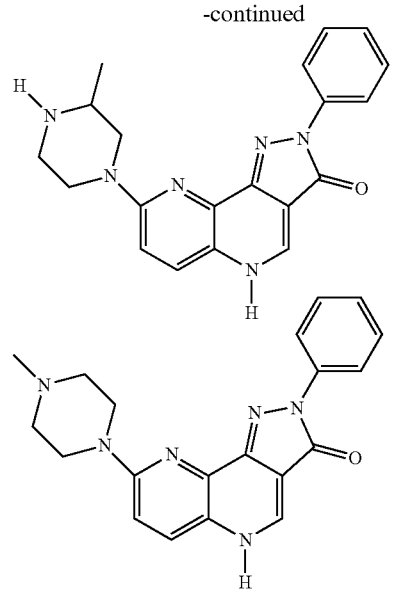

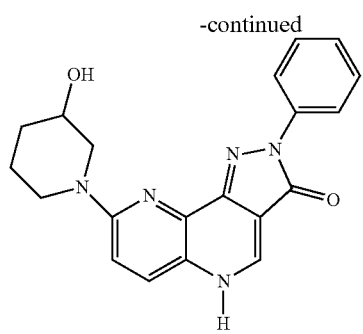
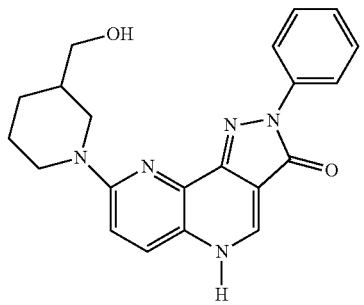
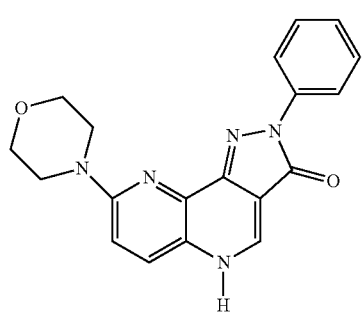
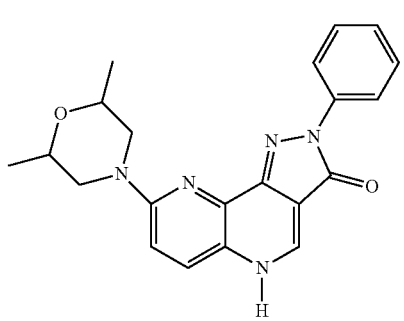
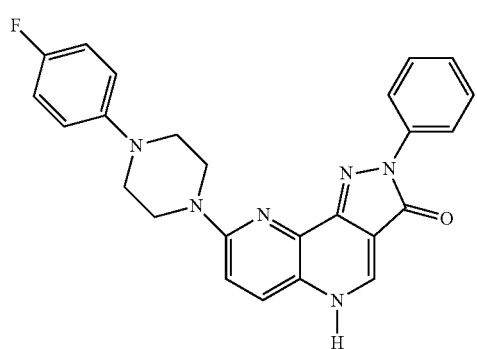
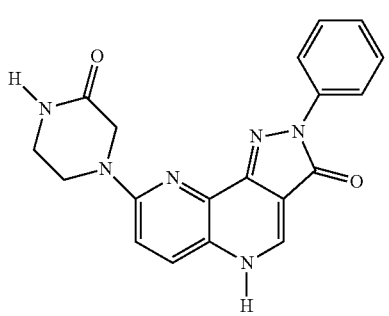
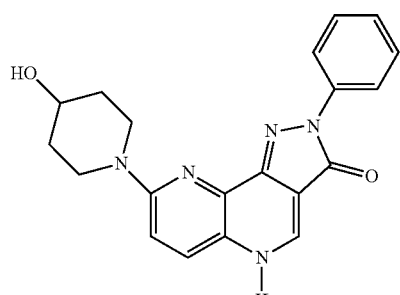
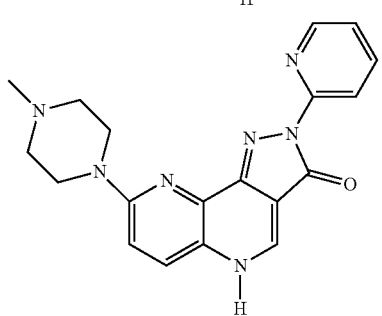
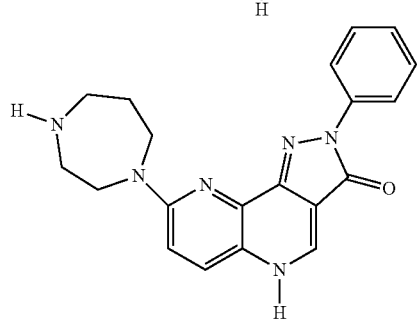
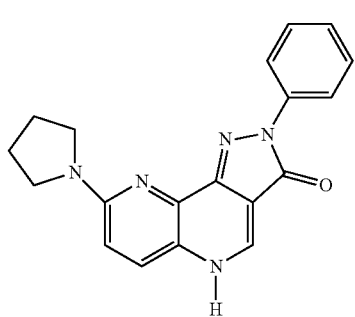

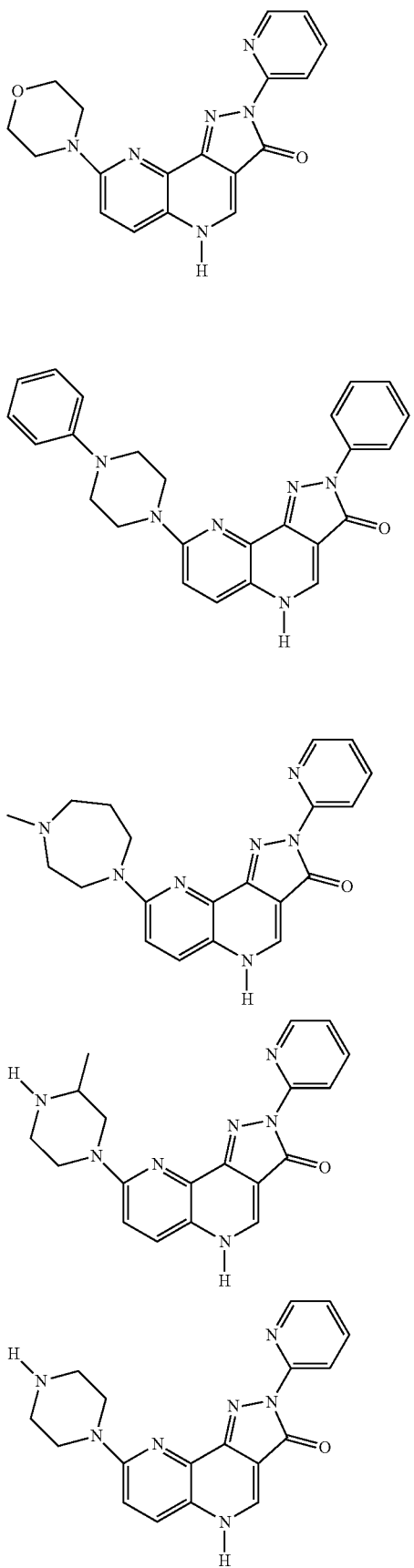

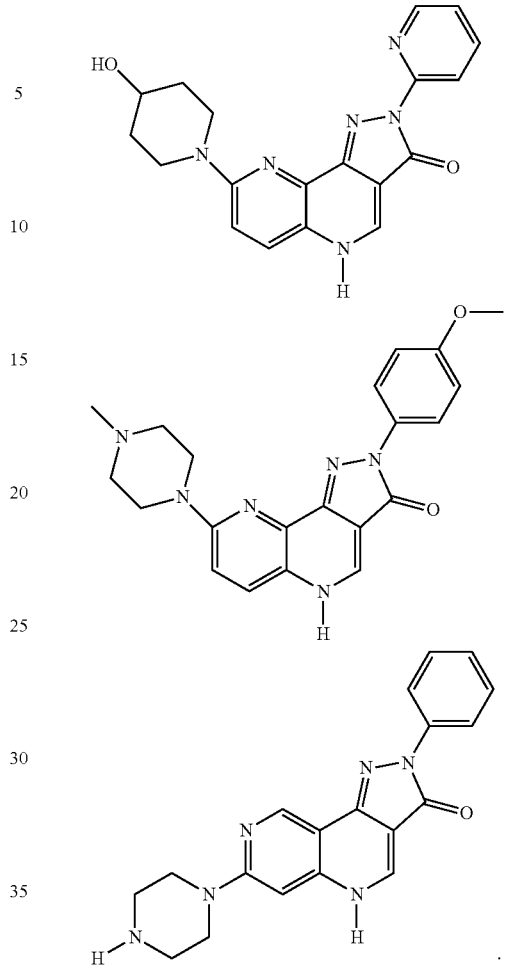

or tautomer thereof, or their pharmaceutically acceptable salts.

The present embodiments provide for a method of modulating one or more GABA$_A$ subtypes in an animal comprising administering to the animal an effective amount of a compound of formula (I):

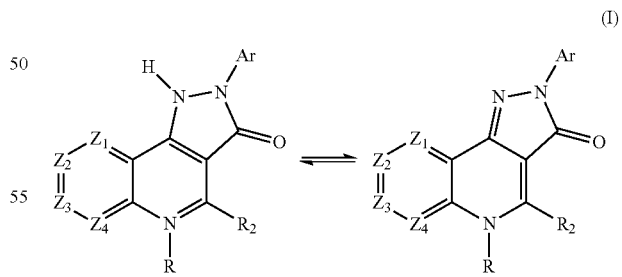

or tautomer thereof, or their pharmaceutically acceptable salts, wherein:

R is absent, hydrogen, or oxide;

$Z_1$, $Z_2$, $Z_3$, and $Z_4$ are each independently N, or C($R_1$), wherein at least one of $Z_1$, $Z_2$, $Z_3$, or $Z_4$ are N and at least two of $Z_1$, $Z_2$, $Z_3$, or $Z_4$ are C($R_1$);

each $R_1$ is independently selected from the group consisting of hydrogen, hydroxy, halo, cyano, $B^1$, —CONR$_a$R$_b$, —$NR_aR_b$, hydroxy($C_1$-$C_6$)alkyl, aryl, heteroaryl, Heterocycle, amino($C_1$-$C_6$)alkyl, ($C_1$-$C_6$)alkyl optionally substituted with up to 5 fluoro, and ($C_1$-$C_6$)alkoxy optionally substituted with up to 5 fluoro, wherein at least one $R_1$ is $B^1$;

$B^1$ is

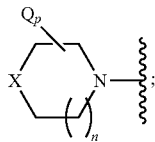

$R_2$ is selected from the group consisting of hydrogen, hydroxy, halo, hydroxy($C_1$-$C_6$)alkyl, ($C_1$-$C_6$)alkyl optionally substituted with up to 5 fluoro, and ($C_1$-$C_6$)alkoxy optionally substituted with up to 5 fluoro;

each $R_a$ and $R_b$ is independently hydrogen, ($C_1$-$C_6$)alkyl, aryl, heteroaryl, heterocycle, ($C_1$-$C_6$)alkylaryl, —S(O)$_z$($C_1$-$C_6$)alkyl, —S(O)$_z$aryl, —C(O)($C_1$-$C_6$)alkyl, —C(O)$NR_g$($C_1$-$C_6$)alkyl, —C(O)$NR_g$aryl, —C(O)O($C_1$-$C_6$)alkyl, arylOC(O)— or arylC(O)—, or $R_a$ and $R_b$ are taken together with the nitrogen to which they are attached to form a heterocycle group optionally substituted with one or more $R_d$; wherein the heterocycle group optionally include one or more groups selected from O (oxygen), S (sulfur), and $NR_c$;

each $R_c$ is independently hydrogen, ($C_2$-$C_6$)alkenyl, ($C_2$-$C_6$)alkynyl, —C(O)O($C_1$-$C_6$)alkyl, —C(O)Oaryl, ($C_1$-$C_6$)alkoxy($C_1$-$C_6$)alkyl, hydroxy($C_1$-$C_6$)alkyl, aryl, heteroaryl, heterocycle, arylO($C_1$-$C_6$)alkyl, —C(O)$NR_g$($C_1$-$C_6$)alkyl, —C(O)$NR_g$aryl, —S(O)$_z$($C_1$-$C_6$)alkyl, —S(O)$_z$aryl, —C(O)($C_1$-$C_6$)alkyl, arylC(O)—, ($C_1$-$C_6$)alkyl optionally substituted with up to 5 fluoro, or ($C_1$-$C_6$)alkoxy optionally substituted with up to 5 fluoro;

each $R_d$ is independently hydrogen, halo, oxo, hydroxy, —C(O)$NR_eR_f$, —$NR_eR_f$, hydroxy($C_1$-$C_6$)alkyl, aryl, aryl($C_1$-$C_6$)alkyl, ($C_1$-$C_6$)alkyl optionally substituted with up to 5 fluoro, or ($C_1$-$C_6$)alkoxy optionally substituted with up to 5 fluoro;

each $R_e$ and $R_f$ is independently selected from hydrogen, ($C_1$-$C_6$)alkyl, aryl, heteroaryl, heterocycle, ($C_1$-$C_6$)alkylaryl, aryl($C_1$-$C_6$)alkyl, —C(O)($C_1$-$C_6$)alkyl, —S(O)$_z$($C_1$-$C_6$)alkyl, —S(O)$_z$$NR_g$($C_1$-$C_6$)alkyl, —S(O)$_z$aryl, —C(O)$NR_g$($C_1$-$C_6$)alkyl, —C(O)($C_1$-$C_6$)alkyl, arylC(O)—, arylOC(O)—, or —C(O)O($C_1$-$C_6$)alkyl;

$R_g$ is hydrogen, aryl, heteroaryl, heterocycle or ($C_1$-$C_6$)alkyl optionally substituted with up to 5 fluoro;

Ar is aryl optionally substituted with one or more M or heteroaryl optionally substituted with one or more M;

each Q is independently hydrogen, halo, oxo, hydroxy, —C(O)$NR_aR_b$, —$NR_aR_b$, ($C_1$-$C_6$)alkyl optionally substituted with up to 5 fluoro, ($C_1$-$C_6$)alkoxy optionally substituted with up to 5 fluoro, ($C_1$-$C_6$)alkyl optionally substituted with one or more $R_d$, hydroxy($C_1$-$C_6$)alkyl optionally substituted with one or more $R_d$, aryl optionally substituted with one or more $R_d$, or aryl($C_1$-$C_6$)alkyl optionally substituted with one or more $R_d$;

each M is independently hydrogen, halo, $CF_3$, $CF_2H$, hydroxy, cyano, nitro, ($C_1$-$C_6$)alkyl, hydroxy($C_1$-$C_6$)alkyl, ($C_1$-$C_6$)alkoxy, —$NR_aR_b$, aryl, hetero aryl or heterocycle;

each X is independently NL, oxygen, C(O)$_2$, or S(O)$_z$;

each L is independently hydrogen, ($C_2$-$C_6$)alkenyl, ($C_2$-$C_6$)alkynyl, —C(O)O($C_1$-$C_6$)alkyl, —C(O)Oaryl, ($C_1$-$C_6$)alkoxy($C_1$-$C_6$)alkyl, hydroxy($C_1$-$C_6$)alkyl, aryl, heteroaryl, heterocycle, arylO($C_1$-$C_6$)alkyl, —CONR$_e$R$_f$, —S(O)$_z$($C_1$-$C_6$)alkyl, —S(O)$_z$aryl, —C(O)($C_1$-$C_6$)alkyl, arylC(O)—, —C(O)$NR_g$($C_1$-$C_6$)alkyl, ($C_1$-$C_6$)alkyl optionally substituted with up to 5 fluoro, or ($C_1$-$C_6$)alkoxy optionally substituted with up to 5 fluoro;

p is an integer selected from 0, 1, 2 and 3;
z is an integer selected from 0, 1 and 2; and
n is an integer selected from 0, 1, and 2.

In one embodiment of the method, the modulation can be negative. In another embodiment, the modulation can be positive.

In one embodiment of the method, the $GABA_A$ subtypes is $GABA_A$ α5. In one embodiment of the method, the modulation can be negative. In another embodiment, the modulation can be positive.

Some embodiments disclosed herein relate to a method of treatment of a cognitive dysfunction in an animal comprising administering to the animal an effective amount of the compounds of the invention, or a pharmaceutically acceptable salt thereof, under conditions wherein the cognitive dysfunction is treated. In one embodiment, the animal is an aged animal. In another embodiment, the cognitive dysfunction is Alzheimer's disease, dementia or another neurodegenerative disease.

Some embodiments disclosed herein relate to a method of treatment of a psychiatric disorder in an animal comprising administering to the animal an effective amount of the compounds of the invention, or a pharmaceutically acceptable salt thereof, under conditions wherein the psychiatric disorder is treated.

Some embodiments disclosed herein relate to the use of the compounds of this invention, or a pharmaceutically acceptable salt thereof, for the manufacture of a medicament useful for modulation of one or more $GABA_A$ subtypes in an animal. In one embodiment of the method, the modulation can be negative. In another embodiment, the modulation can be positive. In one embodiment of the method, the $GABA_A$ subtypes is $GABA_A$ α5. In one embodiment of the method, the modulation can be negative. In another embodiment, the modulation can be positive.

Some embodiments disclosed herein relate to the use of the compounds of this invention, or a pharmaceutically acceptable salt thereof, for the manufacture of a medicament useful for treatment of a cognitive dysfunction in an animal. In one embodiment, the animal is a healthy animal. In another embodiment, the animal is an aged animal. In another embodiment, the cognitive dysfunction is Alzheimer's disease, dementia or another neurodegenerative disease.

Some embodiments disclosed herein relate to the use of the compounds of this invention, or a pharmaceutically acceptable salt thereof, for the manufacture of a medicament useful for treatment of psychiatric disorders in an animal. In one embodiment the psychiatric disorder is an anxiety disorder, sleep disorder, depression, or schizophrenia.

Some embodiments disclosed herein relate to the use of a compound of formula (I), or a pharmaceutically acceptable salt thereof, for the manufacture of a medicament useful for treatment of disorders ameliorated by modulation of $GABA_A$ α subunits other than α5 in an animal. In one embodiment, the modulation can be positive. In another embodiment, the modulation can be negative.

Some embodiments disclosed herein relate to a method of increasing cognitive function in an animal comprising administering to the animal an effective amount of a compound of formula (I), or a pharmaceutically acceptable salt thereof, under conditions wherein memory is increased. In one embodiment, the animal is healthy. In one embodiment, the memory is long term memory. In one embodiment, the memory is short term memory.

Some embodiments disclosed herein relate to the use of a compound of formula (I), or a pharmaceutically acceptable salt thereof, for the manufacture of a medicament for increasing cognitive function in an animal wherein the $GABA_A$ α5 subtype in the animal is negatively modulated. In one embodiment, the animal is healthy. In one embodiment, the memory is long term memory. In one embodiment, the memory is short term memory.

DETAILED DESCRIPTION OF THE INVENTION

| | |
|---|---|
| Ac | Acetyl |
| aq. | Aqueous |
| Bu | n-Butyl |
| cat. | Catalytic |
| CDI | 1,1'-carbonyldiimidazole |
| ° C. | Temperature in degrees Centigrade |
| Dowtherm ® | eutectic mixture of diphenyl ether and biphenyl |
| DBN | 1,5-Diazabicyclo[4.3.0]non-5-ene |
| DBU | 1,8-Diazabicyclo[5.4.0]undec-7-ene |
| DIEA | Diisopropylethylamine |
| DMA | Dimethylacetamide |
| DMF | N,N'-Dimethylformamide |
| DMSO | Dimethylsulfoxide |
| Et | Ethyl |
| g | Gram(s) |
| h | Hour (hours) |
| HPLC | High performance liquid chromatography |
| iPr or isopr | Isopropyl |
| LCMS | Liquid chromatography-mass spectrometry |
| Me | Methyl |
| MeOH | Methanol |
| mL | Milliliter(s) |
| Pd/C | Palladium on activated carbon |
| ppt | Precipitate |
| rt | Room temperature |
| TEA | Triethylamine |
| Tert, t | tertiary |
| μL | Microliter(s) |

As used herein, the term "alkyl" refers to an aliphatic hydrocarbon group. The alkyl moiety may be a "saturated alkyl" group, which means that it does not contain any alkene or alkyne moieties. An "alkene" moiety refers to a group consisting of at least two carbon atoms and at least one carbon-carbon double bond, and an "alkyne" moiety refers to a group consisting of at least two carbon atoms and at least one carbon-carbon triple bond. The alkyl moiety may be branched, straight chain, or cyclic. Examples of branched alkyl groups include, but are not limited to, isopropy, sec-butyl, t-butyl and the like. Examples of straight chain alkyl groups include, but are not limited to, methyl, ethyl, propyl, butyl, pentyl, hexyl, heptyl, and the like. Examples of cyclic alkyl groups include, but are not limited to, cyclopropyl, cyclopentyl, cyclohexyl, cycloheptyl, and the like.

The term "alkoxy" used herein refers to straight or branched chain alkyl radical covalently bonded to the parent molecule through an —O— linkage. Examples of alkoxy groups include, but are not limited to, methoxy, ethoxy, propoxy, isopropoxy, butoxy, n-butoxy, sec-butoxy, t-butoxy and the like.

The term "alkenyl" used herein refers to a monovalent straight or branched chain radical of from two to twenty carbon atoms containing a carbon double bond including, but not limited to, 1-propenyl, 2-propenyl, 2-methyl-1-propenyl, 1-butenyl, 2-butenyl, and the like.

The term "alkynyl" used herein refers to a monovalent straight or branched chain radical of from two to twenty carbon atoms containing a carbon triple bond including, but not limited to, 1-propynyl, 1-butynyl, 2-butynyl, and the like.

The term "aryl" used herein refers to homocyclic aromatic radical whether one ring or multiple fused rings. Moreover, the term "aryl" includes fused ring systems wherein at least two aryl rings, or at least one aryl and an ortho-fused bicyclic carbocyclic radical having about nine to ten ring atoms in which at least one ring is aromatic share at least one chemical bond. Examples of "aryl" rings include, but are not limited to, optionally substituted phenyl, biphenyl, naphthalenyl, phenanthrenyl, anthracenyl, tetralinyl, fluorenyl, indenyl, and indanyl.

The term, "heterocycle" or "heterocycle group" used herein refers to an optionally substituted monocyclic, bicyclic, or tricyclic ring system comprising at least one heteroatom in the ring system backbone. The heteroatoms are independently selected from oxygen, sulfur, and nitrogen. The term, "heterocycle" includes multiple fused ring systems. Moreover, the term "heterocycle" includes fused ring systems that may have any degree of saturation provided that at least one ring in the ring system is not aromatic. The monocyclic, bicyclic, or tricyclic ring system may be substituted or unsubstituted, and can be attached to other groups via any available valence, preferably any available carbon or nitrogen. Preferred monocyclic ring systems are of 4, 5, 6, 7, or 8 members. Six membered monocyclic rings contain from up to three heteroatoms wherein each heteroatom is individually selected from oxygen, sulfur, and nitrogen, and wherein when the ring is five membered, preferably it has one or two heteroatoms wherein each heteroatom is individually selected from oxygen, sulfur, and nitrogen. Preferred bicyclic cyclic ring systems are of 8 to 12 members and include spirocycles. An example of an optional substituent includes, but is not limited to, oxo (=O).

The term "heteroaryl" used herein refers to an aromatic heterocyclic group, whether one ring or multiple fused rings. In fused ring systems, the one or more heteroatoms may be present in only one of the rings. Examples of heteroaryl groups include, but are not limited to, benzothiazyl, benzoxazyl, quinazolinyl, quinolinyl, isoquinolinyl, quinoxalinyl, pyridyl, pyrrolyl, oxazolyl, indolyl, thienyl, and the like. The term "heterocycle" encompasses heteroaryl fused to a non-aromatic ring system.

The term "heteroatom" used herein refers to, for example, oxygen, sulfur and nitrogen.

The term "amino" used herein refers to a nitrogen radical substituted with hydrogen, alkyl, aryl, or combinations thereof. Examples of amino groups include, but are not limited to, —NHMethyl, —NH$_2$, —NMethyl$_2$, —NPhenylMethyl, —NHPhenyl, —NEthylMethyl, and the like.

The term "arylalkyl" used herein refers to one or more aryl groups appended to an alkyl radical. Examples of arylalkyl groups include, but are not limited to, benzyl, phenethyl, phenpropyl, phenbutyl, and the like.

The term "heteroarylalkyl" used herein refers to one or more heteroaryl groups appended to an alkyl radical. Examples of heteroarylalkyl include, but are not limited to, pyridylmethyl, furanylmethyl, thiopheneylethyl, and the like.

The term "aryloxy" used herein refers to an aryl radical covalently bonded to the parent molecule through an —O— linkage.

The term "alkylthio" used herein refers to straight or branched chain alkyl radical covalently bonded to the parent molecule through an —S— linkage.

The term "carbonyl" used herein refers to C=O (i.e. carbon double bonded to oxygen).

The term "oxo" used herein refers to =O (i.e. double bond to oxygen). For example, cyclohexane substituted with "oxo" is cyclohexanone.

The term "alkanoyl" used herein refers to a "carbonyl" substituted with an "alkyl" group, the "alkanoyl" group is covalently bonded to the parent molecule through the carbon of the "carbonyl" group. Examples of alkanoyl groups include, but are not limited to, methanoyl, ethanoyl, propanoyl, and the like. Methanoyl is commonly known as acetyl.

As used herein, a radical indicates species with a single, unpaired electron such that the species containing the radical can be covalently bonded to another species. Hence, in this context, a radical is not necessarily a free radical. Rather, a radical indicates a specific portion of a larger molecule. The term "radical" can be used interchangeably with the term "group."

As used herein, a substituted group is derived from the unsubstituted parent structure in which there has been an exchange of one or more hydrogen atoms for another atom or group.

Asymmetric carbon atoms may be present in the compounds described. All such isomers, including diastereomers and enantiomers, as well as the mixtures thereof are intended to be included in the scope of the recited compound. In certain cases, compounds can exist in tautomeric forms. All tautomeric forms are intended to be included in the scope Likewise, when compounds contain an alkenyl or alkenylene group, there exists the possibility of cis- and trans-isomeric forms of the compounds. Both cis- and trans-isomers, as well as the mixtures of cis- and trans-isomers, are contemplated. Thus, reference herein to a compound includes all of the aforementioned isomeric forms unless the context clearly dictates otherwise.

Various forms are included in the embodiments, including polymorphs, solvates, hydrates, conformers, salts, and prodrug derivatives. A polymorph is a composition having the same chemical formula, but a different structure. A solvate is a composition formed by solvation (the combination of solvent molecules with molecules or ions of the solute). A hydrate is a compound formed by an incorporation of water. A conformer is a structure that is a conformational isomer. Conformational isomerism is the phenomenon of molecules with the same structural formula but different conformations (conformers) of atoms about a rotating bond. Salts of compounds can be prepared by methods known to those skilled in the art. For example, salts of compounds can be prepared by reacting the appropriate base or acid with a stoichiometric equivalent of the compound.

The term "animal" as used herein includes birds, reptiles, and mammals (e.g. domesticated mammals and humans).

The terms "individual," "host," "subject," and "patient" are used interchangeably herein, and refer to a mammal, including, but not limited to, murines, simians, humans, mammalian farm animals, mammalian sport animals, and mammalian pets.

SPECIFIC EMBODIMENTS

In a specific embodiment of the invention, the compound of formula (I) is a compound of any of the formulae Ia-Iw

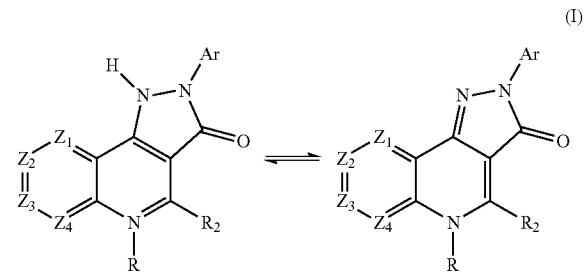

(I)

Specific values listed below for radicals, substituents, and ranges, are for illustration only; they do not exclude other defined values or other values within defined ranges for the radicals and substituents.

A specific value for Ar can be phenyl, 4-methoxyphenyl, or 2-pyridyl.

Designation $B^1$ is intended to mean the group:

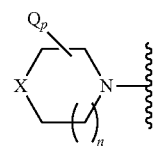

where the $B^1$ group is attached to a ring carbon atom (i.e. C) at a position in the ring to which the bond is attached. The carbon atom may be at the $Z_1$, $Z_2$, $Z_3$ or $Z_4$ position of the ring structure.

A specific value for $B^1$ can be piperazine, pyrrolidine, morpholine, piperidine, and perhydro-1,4-diazepine.

A specific value for X can be carbon, oxygen, or nitrogen.

A specific value of n can be 0, 1, or 2.

A specific value for Q can be hydrogen, $(C_1-C_6)$alkyl, and hydroxy$(C_1-C_6)$alkyl.

The general methods to synthesize these compounds are detailed below.

Process of Preparation

Processes for preparing compounds of formula (I), specifically 6 and 14 are provided as further embodiments of the invention and are illustrated by the following procedures in which the meanings of the generic radicals are as given above unless otherwise qualified.

Compounds of the general formula (I) can be prepared using the general synthetic approach illustrated below in Scheme 1, to access compounds of the type 6 and in Scheme 2, to access compounds of the type 14.

Scheme 1: General Reaction Scheme to Aryl 2,5-dihydro-pyrazolo[4,3-c][1,5]Pyrazolonaphthyridine

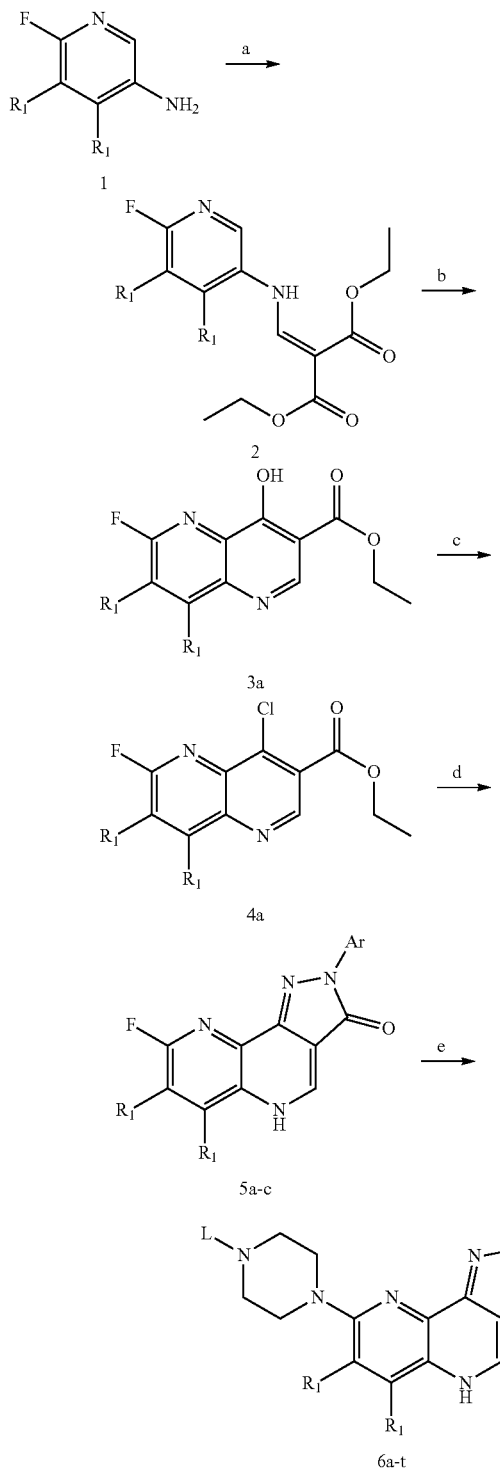

a) 1 equiv. diethyl 2-(ethoxymethylene)malonate, 125° C., 3 hrs, b) Ph₂O, reflux, 30 min-3 hrs, c) 4 equiv. oxalyl chloride, cat. DMF, CHCl₃, reflux, 3 hrs, d) 2 equiv. aryl or heteroaryl hydrazine, 2 equiv. triethylamine, o-xylene, reflux, 12 hrs. e) L-N-piperazine, 175° C., 24-72 hrs.

General Reaction Scheme 1 shows a representative synthetic method for the synthesis of Aryl 2,5-dihydro-pyrazolo[4,3-c][1,5]Pyrazolonaphthyridines. The 3-amino-pyridine of Formula 1 can be reacted with diethyl 2-(ethoxymethylene)malonate under heating to afford, in an addition-elimination type reaction, the enamine of Formula 2. Thermal cyclization of the compound of Formula 2 provides the hydroxyl-azaquinoline of formula 3a. Solvents that can be used in step (b) include but are not limited to diphenyl ether, Dowtherm® and similar high boiling point stable solvents. Conversion of the hydroxyl-azaquinoline of formula 3a to the chloro-azaquinoline of formula 4a can be accomplished using a chlorinating agent in a halogenated solvent and optionally catalytic DMF. Chlorinating agents that can be used in step (c) include but are not limited to oxalyl chloride, P(O)Cl₃, PCl₅, thionyl chloride, phosgene, triphosgene, and similar chlorinating agents. Solvents that can be used in step (c) include but are not limited to chlorobenzene, methylene chloride, 1,2-dichloroethane, chloroform, and similar solvents. The chloro-azaquinoline of formula 4a can be reacted with aryl or heteroaryl hydrazine to form the tricyclic oxo-pyrazole of formula 5a-c. Organic bases that can be used in step (d) include but are not limited to triethyl amine (TEA), diisopropylethyl amine (DIEA), 1,8-Diazabicyclo[5.4.0]undec-7-ene (DBU), 1,5-Diazabicyclo[4.3.0]non-5-ene (DBN), N-methylpiperidine, and the like. Solvents that can be used in step (d) include but are not limited to o-xylene, xylenes, chlorobenzene, toluene, and the like. Displacement of the fluoro of the compound of formula 5a-c with a cyclic amine under heating provides the compound of formula 6a-t. Step (e) can be performed with solvent or neat.

Scheme 2: General Reaction Scheme to Aryl 2,5-dihydro-pyrazolo[4,3-c][1,6]Pyrazolonaphthyridine

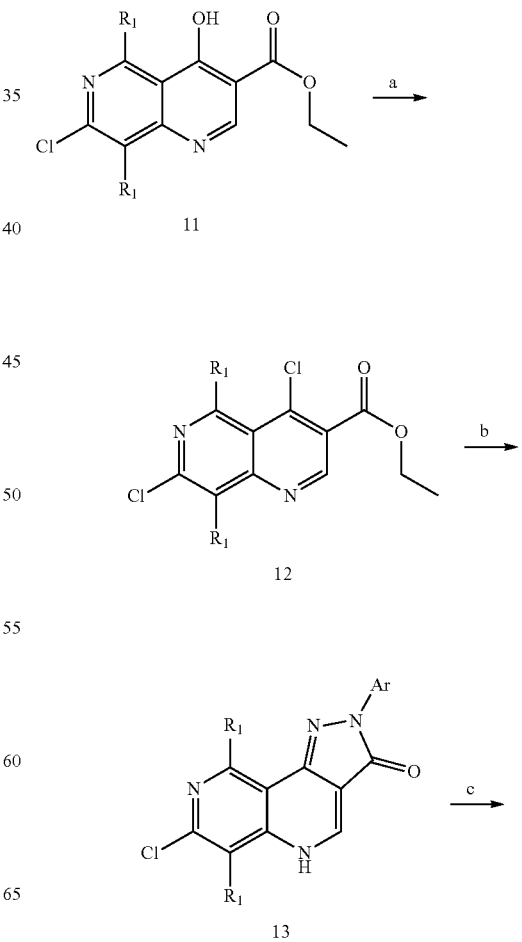

-continued

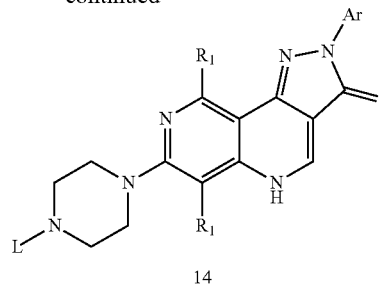

14 a) 4 equiv. oxalyl chloride, cat. DMF, CHCl₃, reflux, 3 hrs, b) 2 equiv. aryl or heteroaryl hydrazine, 2 equiv. triethylamine, o-xylene, reflux, 12 hrs. c) L-N-piperazine, 175° C., 24-72 hrs.

General Reaction Scheme 2 shows a representative synthetic method for the synthesis of Aryl 2,5-dihydro-pyrazolo [4,3-c][1,6]Pyrazolonaphthyridine. Conversion of the hydroxyl-azaquinoline of formula 11 to the chloro-azaquinoline of formula 12 can be accomplished using a chlorinating agent in a halogenated solvent and optionally catalytic DMF. Chlorinating agents that can be used in step (a) include but are not limited to oxalyl chloride, P(O)Cl₃, PCl₅, thionyl chloride, phosgene, triphosgene, and similar chlorinating agents. Solvents that can be used in step (a) include but are not limited to chlorobenzene, methylene chloride, 1,2-dichloroethane, chloroform, and similar solvents. The chloro-azaquinoline of formula 12 can be reacted with aryl or heteroaryl hydrazine to form the tricyclic oxo-pyrazole of formula 13. Organic bases that can be used in step (b) include but are not limited to triethyl amine (TEA), diisopropylethyl amine (DIEA), 1,8-Diazabicyclo[5.4.0]undec-7-ene (DBU), 1,5-Diazabicyclo[4.3.0]non-5-ene (DBN), N-methylpiperidine, and the like. Solvents that can be used in step (b) include but are not limited to o-xylene, xylenes, chlorobenzene, toluene, and the like. Displacement of the chloro of the compound of formula 13 with a cyclic amine under heating provides the compound of formula 14. Step (c) can be performed with solvent or neat.

Method of Synthesis of Pyrazolonaphthyridines

Example 1

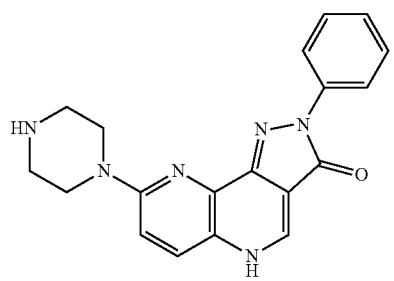

6a

2-Phenyl-8-(piperazin-1-yl)-2,5-dihydro-pyrazolo[4,3-c][1,5]naphthyridin-3-one (6a)

Step 1

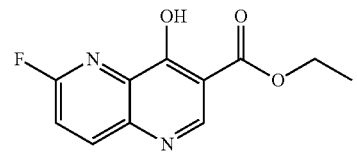

3a

Ethyl-6-fluoro-4-hydroxy-[1,5]naphthyridine-3-carboxylate (3a)

Equimolar quantities of 5-amino-2-fluoropyridine and diethyl 2-(ethoxymethylene)malonate were combined and refluxed for 3 hours at 120° C., Ethanol was removed in vacuo to afford the 2-(4-fluoro-3-pyridyl)-aminomethylene-malonic acid diethyl ester in quantitative yield. The resulting solid was added to refluxing Dowtherm A® and maintained at that temperature for 1 hour. The mixture was cooled to 80° C. and added to ligroin. The solid formed was collected by filtration and washed with hexane to afford product in 30-80% yield. ¹H-NMR (DMSO-d6) δ (ppm): 1.26 (3H, t, J=7.14 Hz), 4.17 (2H, q, J=7.14 Hz), 7.54 (1H, dd, J=9.07, 3.02 Hz), 8.24 (1H, dd, J=8.79, 7.14 Hz), 8.58 (1H, s). m/z 237.3 (MH⁺).

Step 2

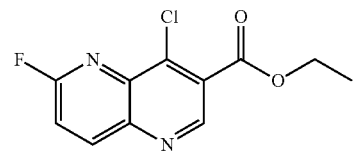

4a

Ethyl-4-chloro-6-fluoro-[1,5]naphthyridine-3-carboxylate (4a)

To a suspension of 3a in chloroform were added 4 equivalents of oxalyl chloride followed by 0.1 equiv. of dimethylformamide. The solution was refluxed for 3 hours and was quenched with 5 M sodium hydroxide solution at 4° C. The chloroform layer was collected, washed with 100 mL water and brine solution, dried over anhydrous sodium sulfate, filtered and concentrated in vacuo. Product was obtained by recrystallization using acetone. ¹H-NMR (CDCl₃) δ (ppm): 1.47 (3H, t, J=7.14 Hz), 4.53 (2H, q, J=7.14 Hz), 7.45 (1H, dd, J=8.79, 3.02 Hz), 8.54 (1H, dd, J=9.06, 7.41), 9.21 (1H, s). m/z 255.7 (MH⁺).

Step 3

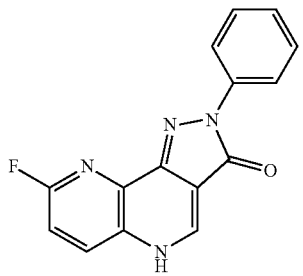

8-Fluoro-2-phenyl-2,5-dihydro-pyrazolo[4,3-c][1,5]naphthyridin-3-one (5a)

In a vial were added 4a, phenyl hydrazine and triethylamine. The vial was sealed and heated to 135° C. for 12 hours. The product was collected by filtration and was washed with methanol in 85% yield. $^1$H-NMR (DMSO-d6) δ (ppm): 7.18 (1H, dd, J=7.41, 7.14 Hz), 7.50 (3H, m), 8.26 (3H, m), 8.81 (1H, s). m/z 281.3 (MH$^+$).

Step 4

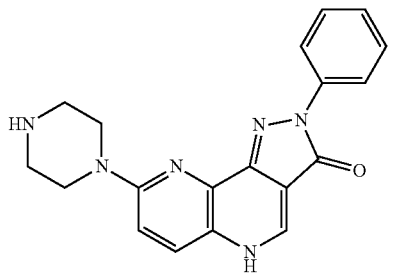

2-Phenyl-8-(piperazin-1-yl)-2,5-dihydro-pyrazolo[4,3-c][1,5]naphthyridin-3-one (6a)

Compound 5a was stirred with excess of piperazine at 175° C. for 24 hours. The precipitates were collected by filtration and washed with ethyl acetate and purified using column chromatography to obtain title compound in 84% yield. $^1$H-NMR (DMSO-d6) δ (ppm): 2.88 (4H, brm), 3.64 (4H, brm), 7.11 (2H, tt, J=7.42, 1.10 Hz), 7.23 (1H, d, J=9.34 Hz), 7.41 (2H, m), 7.84 (1H, d, J=9.06 Hz), 8.22, (2H, m), 8.51 (1H, s). m/z 347.4 (MH$^+$).

Example 2

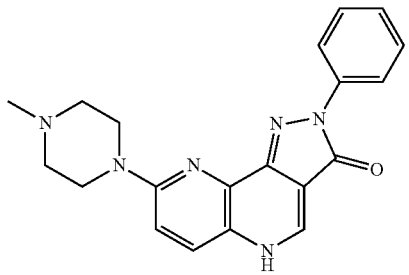

8-(4-Methyl-piperazin-1-yl)-2-phenyl-2,5-dihydro-pyrazolo[4,3-c]-[1,5]naphthyridin-3-one (6b)

The title compound was prepared following the procedure described for 6a using 1-methylpiperazine instead of piperazine. $^1$H-NMR (DMSO-d6) δ (ppm): 2.52 (3H, s), 2.84 (4H, brm), 3.62 (4H, brm), 7.11 (1H, t, J=7.22 Hz), 7.20 (1H, d, J=9.28 Hz), 7.40 (2H, dd, J=8.30, 7.57 Hz), 7.80 (1H, d, J=9.28 Hz), 8.21 (2H, d, J=7.57 Hz), 8.50 (1H, s). m/z 361.4 (MH$^+$).

Example 3

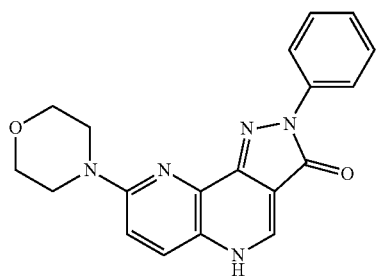

8-Morpholin-4-yl-2-phenyl-2,5-dihydro-pyrazolo[4,3-c][1,5]naphthyridin-3-one (6c)

The title compound was prepared following the procedure described for 6a using morpholine instead of piperazine. $^1$H-NMR (DMSO-d6) δ (ppm): 3.01 (4H, brm), 3.78 (4H, brm), 7.12 (1H, dt, J=7.56, 7.33 Hz), 7.23 (1H, d, J=9.28 Hz), 7.45 (2H, dd, J=8.54, 7.32 Hz), 7.88 (1H, d, J=9.53 Hz), 8.21 (2H, dd, J=8.55, 1.22 Hz), 8.57 (1H, s). m/z 348.4 (MH$^+$).

Example 4

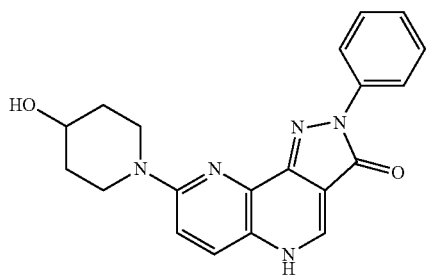

8-(4-Hydroxy-piperidin-1-yl)-2-phenyl-2,5-dihydro-pyrazolo[4,3-c][1,5]naphthyridin-3-one (6d)

The title compound was prepared following the procedure described for 6a using 4-hydroxypiperidine instead of piperazine. $^1$H-NMR (DMSO-d6) δ (ppm): 1.39 (2H, brm), 1.83 (2H, brm), 3.15 (1H, d, J=5.22 Hz), 3.71 (1H, m), 4.19 (2H, m), 4.74 (1H, d, J=4.40 Hz), 7.16 (1H, tt, J=7.40, 1.10 Hz), 7.21 (1H, d, J=9.34 Hz), 7.42 (2H, m), 7.78 (1H, d, J=9.34 Hz), 8.21 (2H, ddd, J=7.69, 1.92, 1.10 Hz), 8.52 (1H, s). m/z 362.4 (MH+).

Example 5

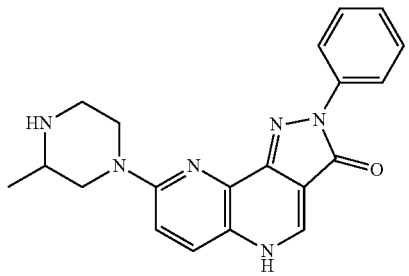

8-(3-Methyl-piperazin-1-yl)-2-phenyl-2,5-dihydro-pyrazolo[4,3-c][1,5]naphthyridin-3-one (6e)

The title compound was prepared following the procedure described for 6a using 2-methylpiperazine instead of piperazine. $^1$H-NMR (DMSO-d6) δ (ppm): 1.00 (3H, s), 2.78 (4H, brm), 3.05 (1H, m), 4.30 (2H, m), 7.07 (2H, m), 7.39 (2H, dd, J=8.24, 7.97 Hz), 7.75 (1H, d, J=9.34 Hz), 8.27 (2H, dd, J=7.42, 1.10 Hz), 8.37 (1H, s). m/z 361.4 (MH+).

Example 6

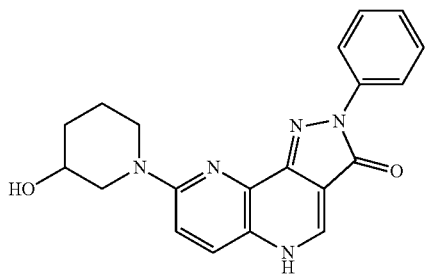

8-(3-Hydroxy-piperidin-1-yl)-2-phenyl-2,5-dihydro-pyrazolo[4,3-c][1,5]naphthyridin-3-one (6f)

The title compound was prepared following the procedure described for 6a using 3-hydroxypiperidine instead of piperazine. $^1$H-NMR (DMSO-d6) δ (ppm): 1.40 (2H, m), 1.75 (1H, m), 1.80 (1H, m), 2.92 (1H, dd, J=12.64, 8.79 Hz), 3.51 (1H, m), 4.10 (1H, m), 4.33 (1H, dd, J=12.63, 3.84 Hz), 4.91 (1H, d, J=4.40 Hz), 7.15 (1H, tt, J=7.42, 1.09 Hz), 7.20 (1H, d, J=9.34 Hz), 7.42 (2H, dd, J=8.52, 7.42 Hz), 7.80 (1H, d, J=9.34 Hz), 8.21 (2H, dd, J=8.79, 1.38 Hz), 8.53 (1H, s). m/z 361.4 (MH+).

Example 7

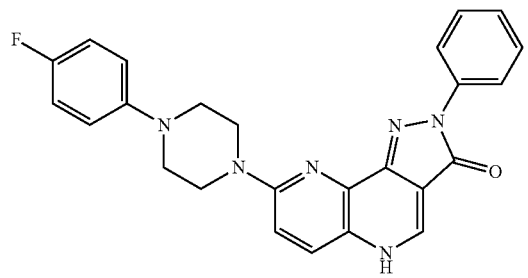

8-[4-(4-Fluoro-phenyl)-piperazin-1-yl]-2-phenyl-2,5-dihydro-pyrazolo[4,3-c][1,5]naphthyridin-3-one (6g)

The title compound was prepared following the procedure described for 6a using 1-(4-fluorophenyl)-piperazine instead of piperazine. $^1$H-NMR (DMSO-d6) δ (ppm): 3.22 (4H, brm), 3.83 (4H, brm), 7.07 (5H, m), 7.32 (1H, d, J=9.34 Hz), 7.43 (2H, dd, J=8.24, 7.69 Hz), 7.85 (1H, d, J=9.34 Hz), 8.19 (2H, dd, J=8.24, 0.82 Hz), 8.57 (1H, s). m/z 441.5 (MH+).

Example 8

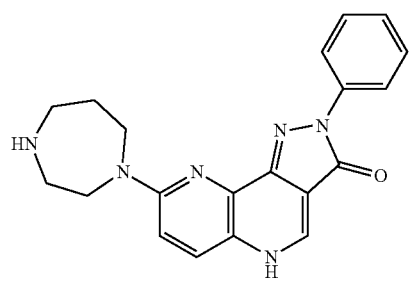

8-[1,4]-Diazepan-1-yl-2-phenyl-2,5-dihydro-pyrazolo[4,3-c][1,5]naphthyridin-3-one (6h)

The title compound was prepared following the procedure described for 6a using perhydro-[1,4]-diazepine instead of piperazine. $^1$H-NMR (DMSO-d6) δ (ppm): 1.82 (2H, m), 2.65 (2H, m), 2.90 (2H, m), 3.88 (4H, m), 6.89 (1H, d, J=9.07 Hz), 7.05 (1H, t, J=7.41 Hz), 7.35 (2H, dd, J=8.52, 7.41 Hz), 7.74 (1H, d, J=9.07 Hz), 8.25 (2H, m), 8.29 (1H, s). m/z 361.4 (MH+).

Example 9

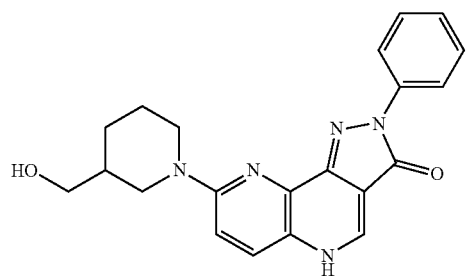

8-(3-Hydroxymethyl-piperidin-1-yl)-2-phenyl-2,5-dihydro-pyrazolo[4,3-c][1,5]naphthyridin-3-one (6i)

The title compound was prepared following the procedure described for 6a using 3-hydroxymethylpiperidine instead of piperazine. $^1$H-NMR (DMSO-d6) δ (ppm): 1.75 (4H, brm), 2.87 (1H, dd, J=12.91, 9.89 Hz), 3.05 (1H, m), 3.13 (1H, d, J=5.22 Hz), 3.54 (2H, brm), 3.88 (2H, brd, J=2.91 Hz), 7.14 (1H, dt, J=7.42, 1.10 Hz), 7.19 (1H, d, J=9.34 Hz), 7.42 (2H, ddd, J=7.41, 2.20, 1.92 Hz), 7.79 (1H, d, J=9.34 Hz), 8.21 (2H, ddd, J=7.69, 1.92, 1.10 Hz), 8.52 (1H, s). m/z 361.4 (MH$^+$).

Example 10

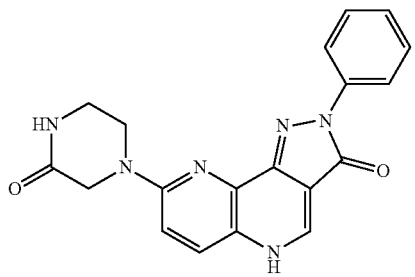

6j 8-(3-Oxo-piperazin-1-yl)-2-phenyl-2,5-dihydro-pyrazolo[4,3-c][1,5]naphthyridin-3-one (6j)

The title compound was prepared following the procedure described for 6a using 2-oxopiperazine instead of piperazine. $^1$H-NMR (DMSO-d6) δ (ppm): 3.08 (2H, m), 3.90 (2H, dd, J=5.67, 4.94), 4.19 (2H, s), 7.15 (1H, dd, J=7.42, 1.09 Hz), 7.20 (1H, d, J=9.34 Hz), 7.40 (2H, dd, J=8.51, 7.42 Hz), 7.85 (1H, d, J=9.06 Hz), 8.16 (1H, br), 8.22 (1H, dd, J=7.70, 1.09 Hz), 8.57 (1H, s). m/z 361.4 (MH$^+$).

Example 11

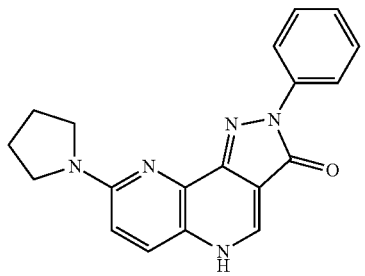

6k

2-Phenyl-8-pyrrolidin-1-yl-2,5-dihydro-pyrazolo[4,3-c][1,5]naphthyridin-3-one (6k)

The title compound was prepared following the procedure described for 6a using pyrrolidine instead of piperazine. $^1$H-NMR (DMSO-d6) δ (ppm): 1.99 (4H, br), 3.49 (4H, br), 6.77 (1H, d, J=9.06 Hz), 7.05 (1H, tt, J=7.41, 0.89 Hz), 7.37 (2H, m), 7.77 (1H, d, J=9.07 Hz), 8.28 (2H, dd, J=7.70, 1.09 Hz), 8.34 (1H, s). m/z 332.4 (MH$^+$).

Example 12

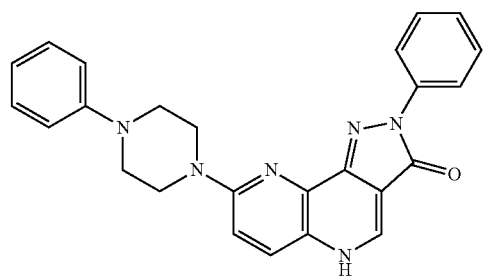

6l

2-Phenyl-8-(4-phenyl-piperazin-1-yl)-2,5-dihydro-pyrazolo[4,3-c][1,5]naphthyridin-3-one (6l)

The title compound was prepared following the procedure described for 6a using 1-phenylpiperazine instead of piperazine. $^1$H-NMR (DMSO-d6) δ (ppm): 2.80 (4H, br), 3.11 (1H, m), 3.80 (1H, dd, J=11.44, 2.75 Hz), 4.39 (1H, J=11.53 Hz), 4.41 (1H, J=11.53 Hz), 7.14 (1H, tt, J=7.42, 1.09 Hz), 7.36 (6H, m), 7.52 (2H, m), 7.83 (1H, d, J=9.34 Hz), 8.16 (2H, m), 8.54 (1H, s). m/z 423.5 (MH$^+$).

Example 13

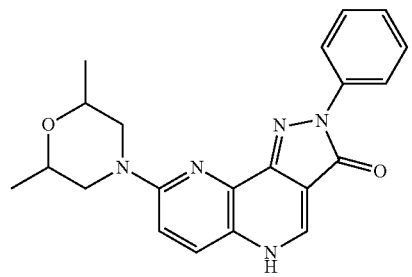

6m 8-(2,6-Dimethyl-morpholin-4-yl)-2-phenyl-2,5-dihydro-pyrazolo[4,3-c][1,5]naphthyridin-3-one (6m)

The title compound was prepared following the procedure described for 6a using 2,6-dimethylmorpholine instead of piperazine. $^1$H-NMR (DMSO-d6) δ (ppm): 1.19 (6H, d, J=7.05 Hz), 2.36 (2H, t, J=12.09, 10.98 Hz), 3.75 (4H, brm), 7.16 (1H, tt, J=7.42, 1.09 Hz), 7.43 (4H, m), 7.56 (2H, d, J=9.06 Hz), 8.23 (2H, dt, J=8.79, 1.37 Hz), 8.56 (1H, s). m/z 376.5 (MH$^+$).

Example 14

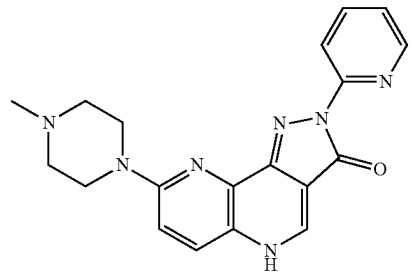

6n 8-(4-Methyl-piperazin-1-yl)-2-pyridin-2-yl-2,5-dihydro-pyrazolo[4,3-c][1,5]naphthyridin-3-one (6n)

Step 1

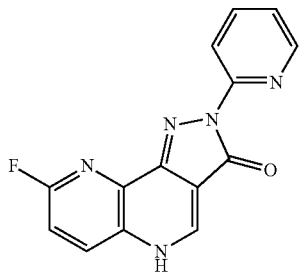

8-Fluoro-2-pyridin-2-yl-2,5-dihydro-pyrazolo[4,3-c][1,5]naphthyridin-3-one (5b)

The title compound was prepared following the procedure described in Step 3 for synthesis for 5a using pyridyl-2-hydrazine instead of phenylhydrazine. $^1$H-NMR (DMSO-d6) δ (ppm): 7.25 (1H, ddd, J=7.14, 4.67, 1.10 Hz), 7.50 (1H, dd, J=8.79, 3.03 Hz), 7.90 (1H, ddd, J=9.34, 7.42, 1.93 Hz), 8.14 (1H, brd, J=8.24 Hz), 8.28 (1H, ddd, J=9.06, 7.42, 7.14 Hz), 8.50 (1H, m), 8.84 (1H, s). m/z 282.3 (MH$^+$).

Step 2

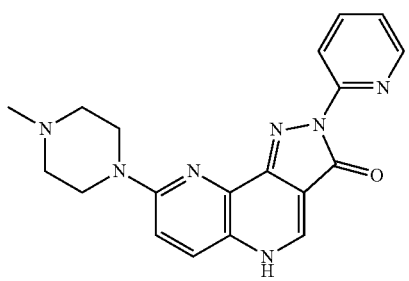

8-(4-Methyl-piperazin-1-yl)-2-pyridin-2-yl-2,5-dihydro-pyrazolo[4,3-c][1,5]naphthyridin-3-one (6n)

The title compound was prepared following the procedure described for 6a using 5b and 1-methylpiperazine instead of 5a and piperazine respectively. $^1$H-NMR (DMSO-d6) δ (ppm): 2.55 (4H, br), 2.77 (3H, brs), 3.80 (4H, br), 7.20 (1H, m), 7.27 (6H, d, J=9.24 Hz), 7.87 (2H, m), 8.20 (1H, d, J=8.24 Hz), 8.48 (1H, m), 8.60 (1H, s). m/z 362.4 (MH$^+$).

Example 15

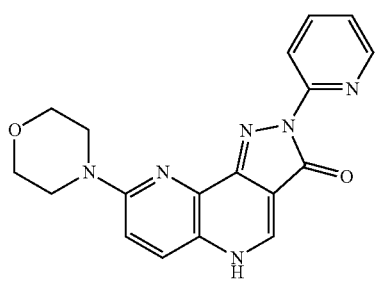

8-Morpholin-4-yl-2-pyridin-2-yl-2,5-dihydro-pyrazolo[4,3-c][1,5]naphthyridin-3-one (6o)

The title compound was prepared following the procedure described for 6a using 5b and morpholine instead of 5a and piperazine respectively. $^1$H-NMR (DMSO-d6) δ (ppm): 3.63 (4H, br), 3.72 (4H, br), 7.19 (2H, m), 7.82 (2H, m), 8.22 (1H, d, J=8.24 Hz), 8.48 (1H, dd, J=2.20, 1.10 Hz), 8.56 (1H, s). m/z 349.4 (MH$^+$).

Example 16

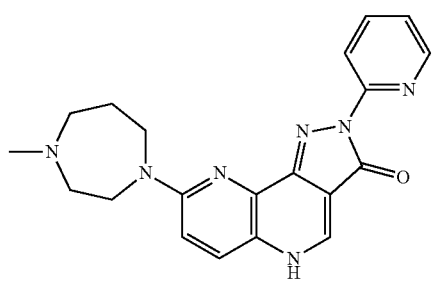

8-(4-Methyl-[1,4]diazepan-1-yl)-2-pyridin-2-yl-2,5-dihydro-pyrazolo[4,3-c][1,5]naphthyridin-3-one (6p)

The title compound was prepared following the procedure described for 6a using 5b and 4-methyl-[1,4]-diazepane instead of 5a and piperazine respectively. $^1$H-NMR (DMSO-d6) δ (ppm): 2.04 (2H, m), 2.35 (3H, s), 2.60 (2H, m), 2.76 (2H, m), 3.76 (2H, d, J=6.32 Hz), 3.98 (2H, t, J=4.67 Hz), 6.96 (1H, d, J=9.36 Hz), 7.25 (1H, ddd, J=7.14, 4.55, 0.82 Hz), 7.82 (1H, d, J=9.34 Hz), 7.92 (1H, m), 8.30 (1H, dt, J=8.24, 0.82 Hz), 8.49 (1H, m), 8.52 (1H, s). m/z 376.4 (MH$^+$).

Example 17

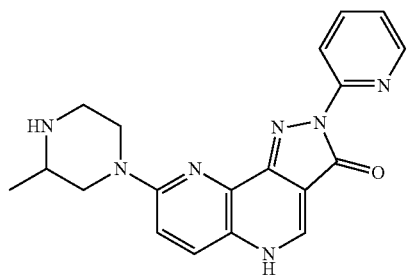

8-(3-Methyl-piperazin-1-yl)-2-pyridin-2-yl-2,5-dihydro-pyrazolo[4,3-c][1,5]naphthyridin-3-one (6q)

The title compound was prepared following the procedure described for 6a using 5b and 2-methylpiperazine instead of 5a and piperazine respectively. $^1$H-NMR (DMSO-d6) δ (ppm): 1.07 (3H, d, J=6.87 Hz), 2.78 (3H, m), 3.00 (2H, m), 4.31 (2H, m), 7.14 (2H, m), 7.83 (2H, m), 8.22 (1H, dt, J=7.96, 7.64 Hz), 8.49 (2H, m). m/z 362.4 (MH$^+$).

Example 18

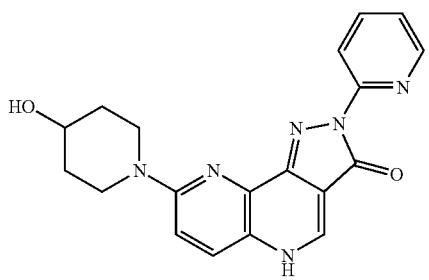

6r

The above compound was prepared following the procedure described for 6a using 5b and 4-hydroxypiperidine instead of piperazine. ¹H-NMR (DMSO-d6) δ (ppm): 2.25 (1H, m), 2.70 (1H, m), 2.89 (2H, m), 3.15 (2H, m), 3.75 (2H, m), 4.74 (1H, m), 7.24 (2H, m), 7.79 (1H, d, J=9.24 Hz), 7.88 (1H, m), 8.23 (1H, d, J=8.24 Hz), 8.49 (1H, dd, J=4.67, 1.10 Hz), 8.53 (1H, s).

Example 19

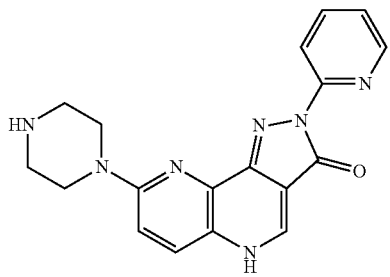

6s 8-piperazin-1-yl-2-pyridin-2-yl-2,5-dihydro-pyrazolo[4,3-c][1,5]naphthyridin-3-one (6s)

The title compound was prepared following the procedure described for 6a using 5b instead of 5a. ¹H-NMR (CDCl₃) δ (ppm): 2.97 (4H, br), 3.72 (4H, br), 6.82 (1H, d, J=9.34 Hz), 7.42 (4H, m), 7.75 (1H, m), 8.17 (2H, d, J=7.97 Hz), 8.52 (1H, s). m/z 348.4 (MH⁺).

Example 20

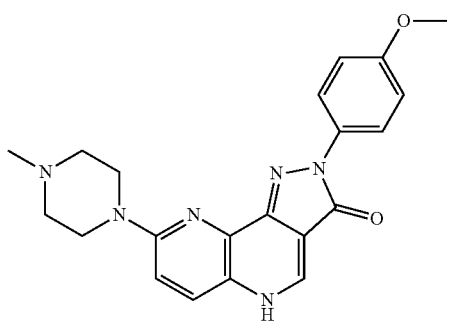

6t 2-(4-Methoxy-phenyl)-8-(4-methyl-piperazin-1-yl)-2,5-dihydro-pyrazolo[4,3-c][1,5]naphthyridin-3-one (6t)

Step 1

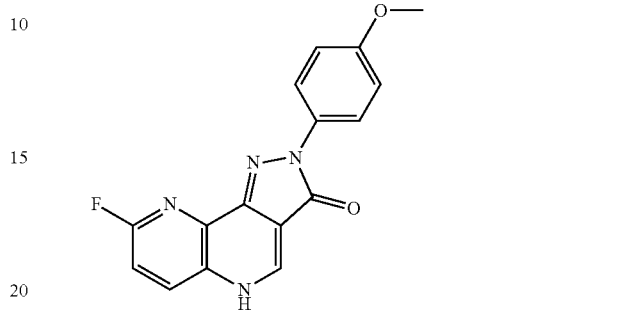

5c

8-Fluoro-2-(4-methoxy-phenyl)-2,5-dihydro-pyrazolo[4,3-c][1,5]naphthyridin-3-one (5c)

The title compound was prepared following the procedure described in Step 3 for synthesis for 5a using 4-methoxyphenylhydrazine instead of phenylhydrazine. ¹H-NMR (DMSO-d6) δ (ppm): 7.25 (1H, ddd, J=7.14, 4.67, 1.10 Hz), 7.50 (1H, dd, J=8.79, 3.03 Hz), 7.90 (1H, ddd, J=9.34, 7.42, 1.93 Hz), 8.14 (1H, brd, J=8.24 Hz), 8.28 (1H, ddd, J=9.06, 7.42, 7.14 Hz), 8.50 (1H, m), 8.84 (1H, s). m/z 282.3 (MH⁺).

Step 2

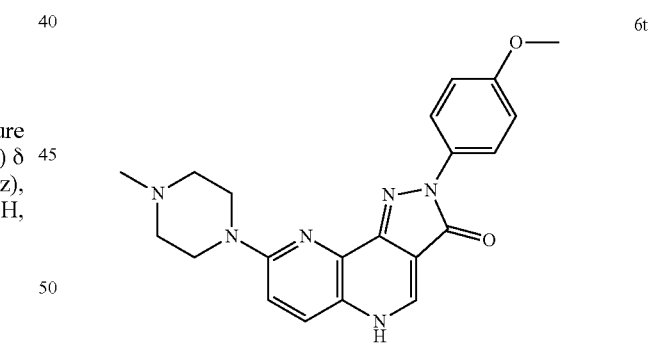

6t 2-(4-Methoxy-phenyl)-8-(4-methyl-piperazin-1-yl)-2,5-dihydro-pyrazolo[4,3-c][1,5]naphthyridin-3-one (6t)

The title compound was prepared following the procedure described for 6a using 5c and 1-methylpiperazine instead of 5a and piperazine respectively. ¹H-NMR (DMSO-d6) δ (ppm): 2.22 (3H, s), 2.56 (4H, m), 3.64 (4H, m), 6.98 (2H, d, J=9.07 Hz), 7.15 (1H, d, J=9.34 Hz), 7.78 (6H, d, J=9.34 Hz), 8.10 (2H, d, J=9.07 Hz), 8.45 (1H, s). m/z 391.4 (MH⁺).

Example 21

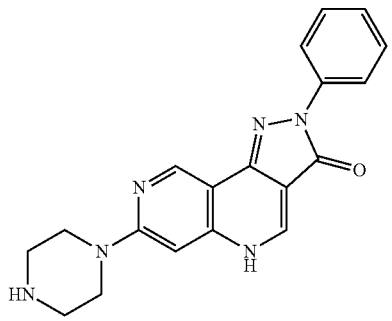

2-Phenyl-7-(piperazin-1-yl)-2,5-dihydro-pyrazolo[4,3-c][1,6]naphthyridin-3-one (14)

Step 1

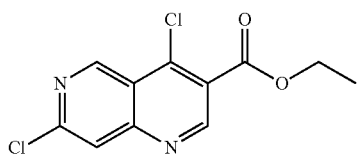

Ethyl-4,7-dichloro-[1,6]naphthyridine-3-carboxyate (12)

The title compound was prepared following the procedure described for 4a using 7-chloro-4-hydroxy-[1,6]naphthyridine-3-carboxylic acid ethyl ester (11). $^1$H-NMR (CDCl$_3$) δ (ppm): 1.47 (3H, t, J=7.14 Hz), 4.53 (2H, q, J=7.14 Hz), 8.02 (1H, s), 9.37 (1H, s), 9.62 (1H, s). m/z 272.2 (MH$^+$).

Step 2

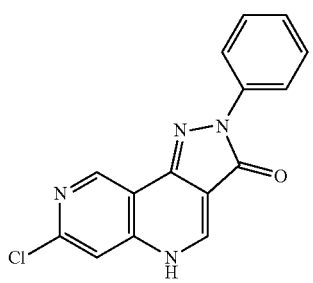

7-Chloro-2-phenyl-2,5-dihydro-pyrazolo[4,3-c][1,6]naphthyridin-3-one (13)

The title compound was prepared following the procedure described in Step 3 for synthesis for 5a using 12 instead of 4a. $^1$H-NMR (DMSO-d6) δ (ppm): 7.18 (1H, dd, J=7.14, 6.59 Hz), 7.46 (2H, dd, J=8.24, 7.70 Hz), 7.60 (1H, s), 8.14 (2H, d, J=7.51 Hz), 8.81 (1H, s), 9.21 (1H, s). m/z 297.7 (MH$^+$).

Step 3

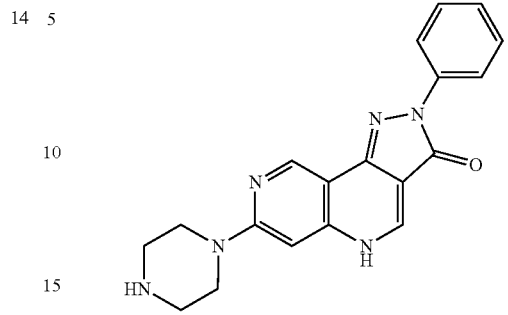

2-Phenyl-7-(piperazin-1-yl)-2,5-dihydro-pyrazolo[4,3-c][1,6]naphthyridin-3-one (14)

The title compound was prepared following the procedure described in Step 4 for synthesis for 6a using 13 instead of 5a. $^1$H-NMR (DMSO-d6) δ (ppm): 2.80 (4H, brm), 3.46 (4H, brm), 6.68 (1H, s), 7.06 (1H, dd, J=7.42, 7.14 Hz), 7.36 (2H, dd, J=8.52, 7.41 Hz), 8.20 (2H, dd, J=8.79, 1.10 Hz), 8.47 (1H, s), 8.94 (1H, s). m/z 347.4 (MH$^+$).

Example 22

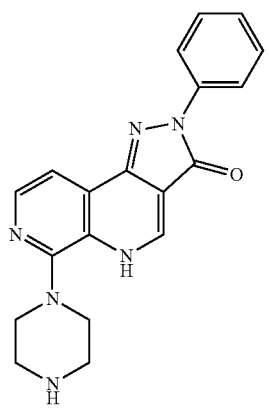

2-Phenyl-6-(piperazin-1-yl)-2,5-dihydro-pyrazolo[4,3-c][1,7]naphthyridin-3-one (17)

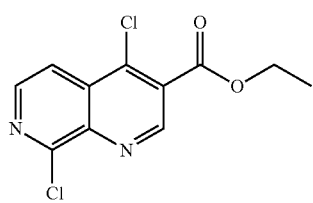

Step 1

Ethyl-4,8-dichloro-[1,7]naphthyridine-3-carboxyate (15)

The title compound was prepared following the procedure described for 4a using 8-chloro-4-hydroxy-[1,7]naphthyridine-3-carboxylic acid ethyl ester (11). $^1$H-NMR (CDCl$_3$) δ (ppm): 1.47 (3H, t, J=7.14 Hz), 4.53 (2H, q, J=7.14 Hz), 8.13 (1H, d, J=5.8 Hz), 8.55 (1H, d, J=5.8 Hz), 9.35 (1H, s). m/z 271.0 (MH$^+$).

Step 2

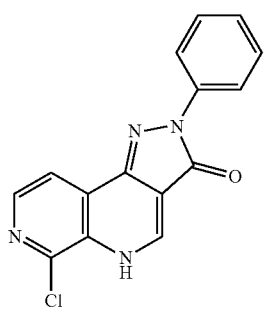

16

6-Chloro-2-phenyl-2,5-dihydro-pyrazolo[4,3-c][1,7]naphthyridin-3-one (16)

The title compound was prepared following the procedure described in Step 3 for synthesis for 5a using 15 instead of 4a. $^1$H-NMR (DMSO-d6) δ (ppm): 7.16 (1H, m), 7.44 (2H, dd, J=8.6, 7.6 Hz), 8.09 (1H, d, J=5.3 Hz), 8.14 (2H, dd, J=8.5, 1.1 Hz), 8.37 (1H, d, J=5.2 Hz), 8.51 (1H, s). m/z 297.7 (MH$^+$).

Step 3

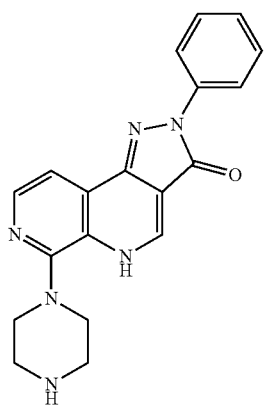

17

2-Phenyl-6-(piperazin-1-yl)-2,5-dihydro-pyrazolo[4,3-c][1,7]naphthyridin-3-one (17)

The title compound was prepared following the procedure described in Step 4 for synthesis for 6a using 16 instead of 5a. $^1$H-NMR (DMSO-d6) δ (ppm): 3.2 (4H, brm), 3.48 (4H, brm), 7.13 (1H, m), 7.46 (2H, m), 7.78 (1H, d, J=5.2 Hz), 8.18 (2H, d, J=7.7 Hz), 8.30 (1H, d, J=5.2 Hz), 8.50 (1H, s). m/z 347.4 (MH$^+$).

Example 23

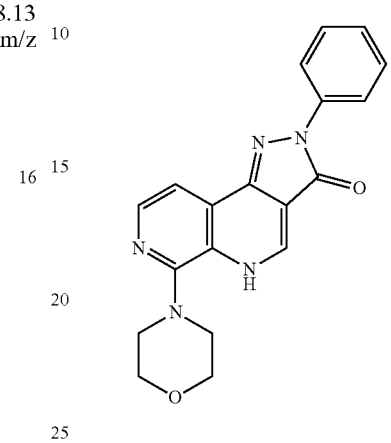

18

6-(Morpholin-4-yl)-2-phenyl-2,5-dihydro-pyrazolo[4,3-c][1,7]naphthyridin-3-one (18)

The title compound was prepared following the procedure described in Step 4 for synthesis for 6a using 16 and morpholine. $^1$H-NMR (DMSO-d6) δ (ppm): 3.17 (4H, brm), 3.87 (4H, brm), 7.15 (1H, m), 7.43 (2H, m), 7.76 (1H, d, J=5.5 Hz), 8.17 (2H, d, J=8.8 Hz), 8.33 (1H, d, J=5.2 Hz), 8.44 (1H, s). m/z 348.1 (MH$^+$).

BIOLOGICAL EXAMPLES

The ability of a compound disclosed herein to act as ligand to the benzodiazepine site of GABA$_A$ can be determined using pharmacological models which are well known in the art using the following assay. The IC$_{50}$ values for the exemplified compounds range from sub nM to 10 μM in a 3-concentration dose response curve.

Benzodiazepine Binding Assay

Whole brain (except cerebellum) of male Wistar derived rats weighing 175±25 g were used to prepare GABA$_A$ central benzodiazepine receptor in Na—K phosphate buffer pH 7.4. A 5 mg aliquot was incubated with 1 nM ($^3$H)-flunitrazepam for 60 minutes at 25° C. Experiments were performed in the presence or absence of 30 μM of GABA. Non-specific binding was estimated in the presence of 10 μM of diazepam. Membranes were filtered and washed, the filters were then counted to determine ($^3$H)-flunitrazepam specifically bound. Test compounds were tested in duplicate according to the required concentrations (Damm, H. W., et al. (1978) *Res. Comm. Chem. Pathol. Pharmacol.* 22: 597-560 incorporated herein in its entirety; Speth, R. C., et al. (1979) *Life Sci.* 24: 351-357 incorporated herein in its entirety).

Examples of Activity:

wherein:

A indicates an IC$_{50}$ of >1 μM

B indicates an IC$_{50}$ of <1 μM

C indicates an IC$_{50}$ of <1 nM

TABLE 1

| No. | Structure | BZ binding assay (IC$_{50}$) | EP result |
|-----|-----------|------------------------------|-----------|
| 6a  | 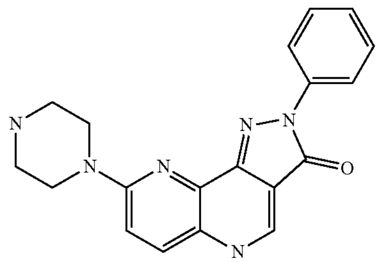          | B | Neg |
| 6b  | 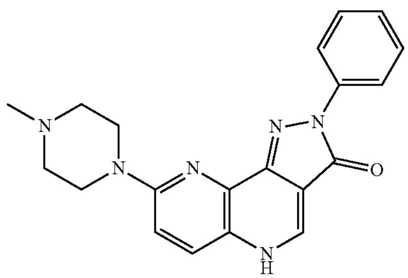          | B | Neg |
| 6c  | 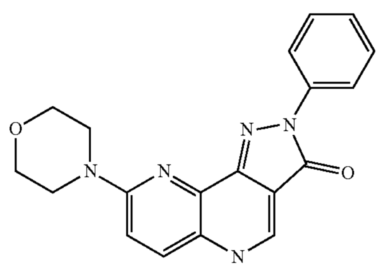 [SMILES: O=c1c2c[nH]c3ccc(N4CCNCC4)nc3c-2nn1-c1ccccc1]          | C | Neg |
| 6d  | 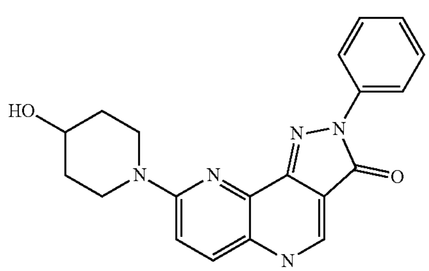 [SMILES: O=c1c2c[nH]c3ccc(N4CCC(O)CC4)nc3c-2nn1-c1ccccc1]          | C |     |
| 6e  | 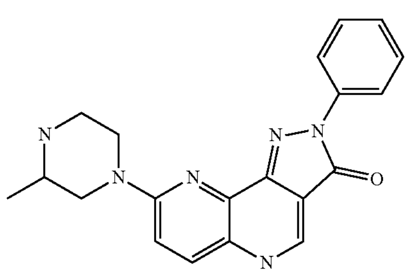 [SMILES: CC1CN(c2ccc3[nH]cc4c(=O)n(-c5ccccc5)nc-4c3n2)CCN1]          | B |     |

TABLE 1-continued
| No. | Structure | BZ binding assay (IC$_{50}$) | EP result |
|---|---|---|---|
| 6f | 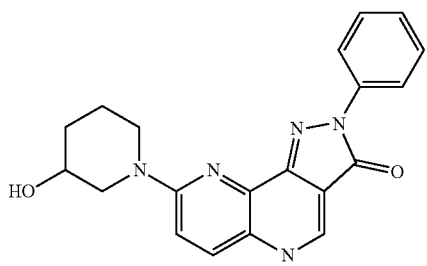 [SMILES: O=c1c2c[nH]c3ccc(N4CCCC(O)C4)nc3c-2nn1-c1ccccc1] | | B |
| 6g | 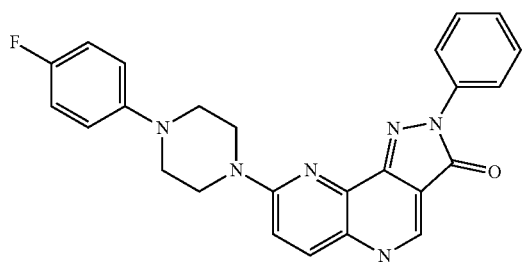 [SMILES: O=c1c2c[nH]c3ccc(N4CCN(c5ccc(F)cc5)CC4)nc3c-2nn1-c1ccccc1] | | B |
| 6h | 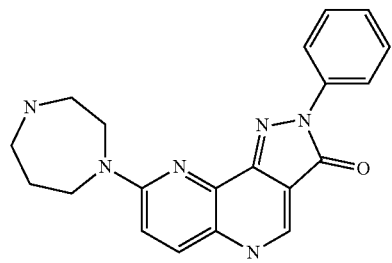 [SMILES: O=c1c2c[nH]c3ccc(N4CCCNCC4)nc3c-2nn1-c1ccccc1] | | B |
| 6i | 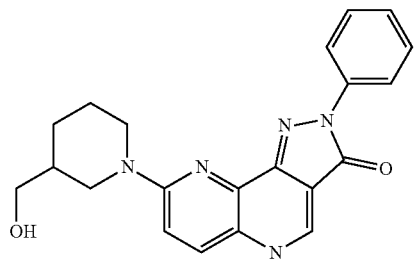 [SMILES: O=c1c2c[nH]c3ccc(N4CCCC(CO)C4)nc3c-2nn1-c1ccccc1] | | C |
| 6j | 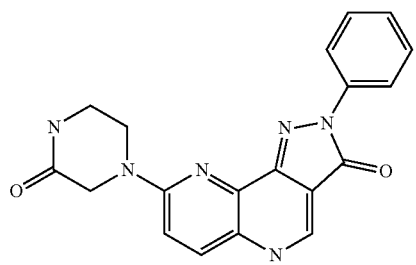 [SMILES: O=C1CN(c2ccc3[nH]cc4c(=O)n(-c5ccccc5)nc-4c3n2)CCN1] | | B |

TABLE 1-continued

| No. | Structure | BZ binding assay (IC$_{50}$) | EP result |
|---|---|---|---|
| 6k | 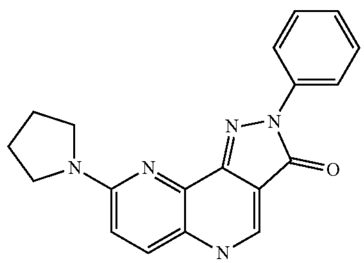 [SMILES: O=c1c2c[nH]c3ccc(N4CCCC4)nc3c-2nn1-c1ccccc1] | C | |
| 6l | 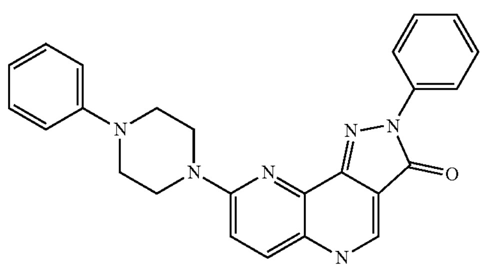 [SMILES: O=c1c2c[nH]c3ccc(N4CCN(c5ccccc5)CC4)nc3c-2nn1-c1ccccc1] | B | Pos |
| 6m | 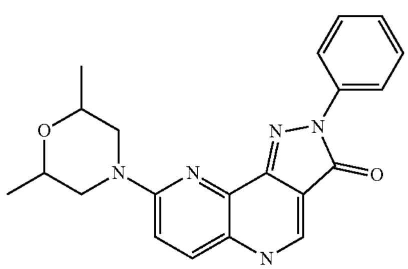 [SMILES: CC1CN(c2ccc3[nH]cc4c(=O)n(-c5ccccc5)nc-4c3n2)CC(C)O1] | B | Pos |
| 6n | 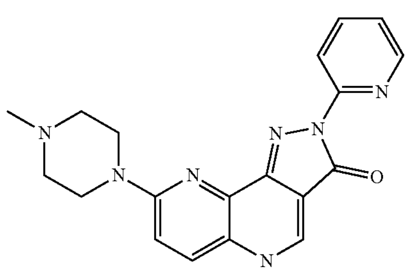 [SMILES: CN1CCN(c2ccc3[nH]cc4c(=O)n(-c5ccccn5)nc-4c3n2)CC1] | B | |
| 6o | 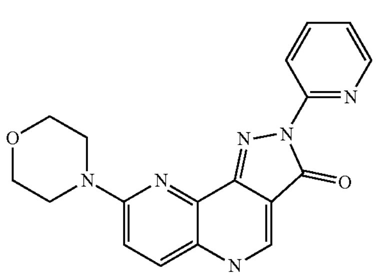 [SMILES: O=c1c2c[nH]c3ccc(N4CCOCC4)nc3c-2nn1-c1ccccn1] | B | |

TABLE 1-continued

| No. | Structure | BZ binding assay (IC$_{50}$) | EP result |
|---|---|---|---|
| 6p | 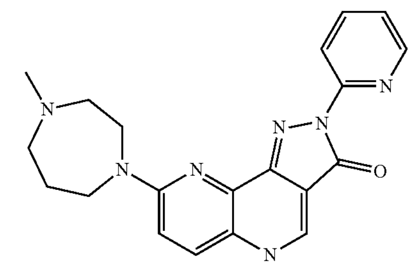 [SMILES: CN1CCCN(c2ccc3[nH]cc4c(=O)n(-c5ccccn5)nc-4c3n2)CC1] | B | |
| 6q | 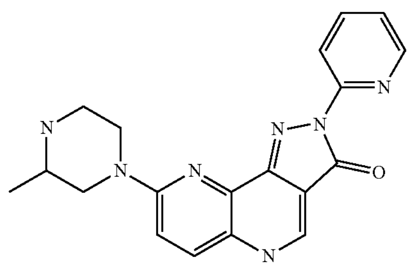 [SMILES: CC1CN(c2ccc3[nH]cc4c(=O)n(-c5ccccn5)nc-4c3n2)CCN1] | B | Pos |
| 6r | 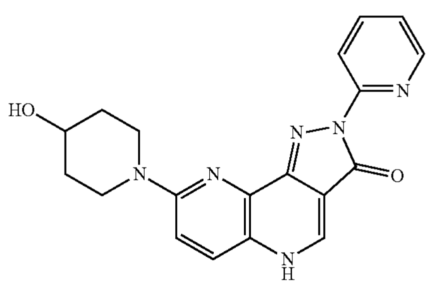 [SMILES: O=c1c2c[nH]c3ccc(N4CCC(O)CC4)nc3c-2nn1-c1ccccn1] | C | |
| 6s | 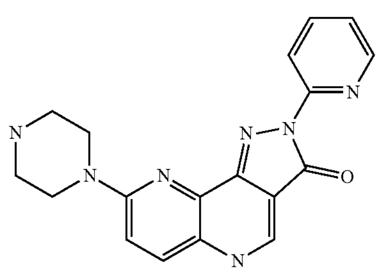 [SMILES: O=c1c2c[nH]c3ccc(N4CCNCC4)nc3c-2nn1-c1ccccn1] | B | Pos |
| 6t | 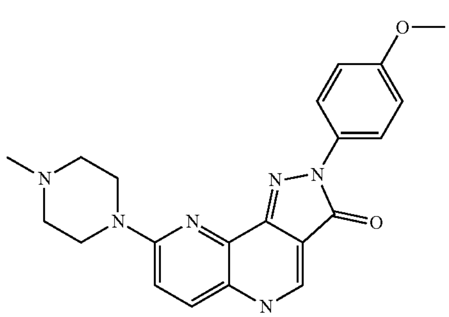 | C | Neg |

TABLE 1-continued

| No. | Structure | BZ binding assay (IC$_{50}$) | EP result |
|---|---|---|---|
| 14 | 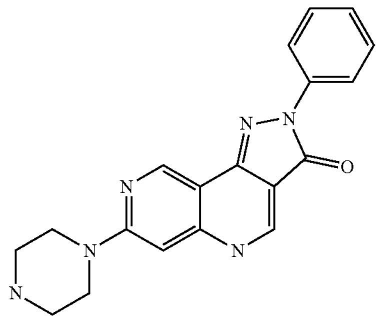 [SMILES: O=c1c2c[nH]c3cc(N4CCNCC4)ncc3c-2nn1-c1ccccc1] | A | Neg |
| 17 | 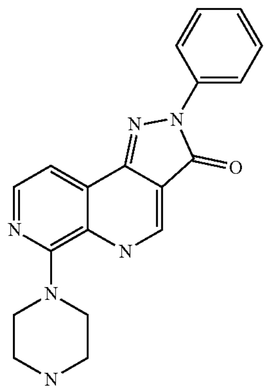 [SMILES: O=c1c2c[nH]c3c(N4CCNCC4)nccc3c-2nn1-c1ccccc1] | A | |
| 18 | 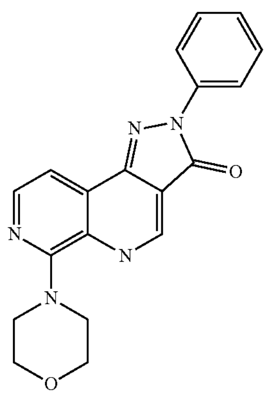 [SMILES: O=c1c2c[nH]c3c(N4CCOCC4)nccc3c-2nn1-c1ccccc1] | | |

All compounds disclosed in Table 1 are assumed to be drawn as neutral. If not indicated, a hydrogen atom is assumed to be present on nitrogen atoms to provide a neutral compound. The compounds of Table 1 can exist in additional isomeric forms, for example, the compounds can exist as tautomers of the drawn structures. The compounds disclosed in Table 1 encompass all possible tautomers of the drawn structures. One of skill in the art will understand that a compound can exist in different tautomeric forms or mixtures there of depending on the environment encompassing the compound, that is an equilibrium can exist between the different tautomerics forms of the compounds and the equilibrium between said forms can be influenced by outside factors.

The modulation of GABA$_A$ function is determined by changes in current as determined in an electrophysiology assay, as is detailed below.

Electrophysiology Assay
Preparation of RNA mRNA was prepared from lyophilized plasmid pellets containing cDNA inserts encoding the specific GABA$_A$ receptor subunit. cDNAs encoding the α2, α3, and γ3 subunits were subcloned into pBluescript, SK⁻. cDNAs encoding the α1 and α5 subunits were subcloned into prC while cDNA encoding the β2 subunit was subcloned into pcDNA1. The cDNA construct encoding the γ2s subunit is in the pGH19 expression construct. Overnight cultures of transformed DH5a bacterial cells were performed to grow sufficient quantities for maxiprep isolation of the plasmid cDNA. The resulting plasmid cDNA was linearized by digestion with an appropriate restriction enzyme that cleaves distal to the cDNA insert (XbaI for α1,2, β2, and γ3 or NotI for α3,5 and γ2, respectively). Following digestion, plasmid cDNA was treated with proteinase K and extracted with phenol/chloroform/isoamyl alcohol, followed by ethanol precipitation. cDNA quality was assessed by agarose-gel electrophoresis (1.5% agarose gel). Samples were stored at −20° C. until use. In vitro transcription was performed with T7 RNA polymerase. mRNA was then stored at −80° C. until use. Plasmids were linearized with appropriate restriction enzymes before in vitro transcription using the Message Machine kit (Ambion, Austin, Tex.).

GABA$_A$ Receptor Expression in *Xenopus oocytes*.

GABA$_A$ receptor expression in *Xenopus oocytes*: Following 45 min of 0.15% Tricaine anesthesia, an ovarian section containing the follicular oocytes was removed from the frog through a lateral abdominal incision. Oocytes were immediately placed in a calcium-free solution (NaCl 96 mM, MgCl$_2$ 1 mM, KCl 2 mM, Hepes 50 mM, pyruvate 2.5 mM, gentamycin 100 μg/mL, penicillin-streptomycin 50 U/mL, pH 7.4). Following 1.5-2 hour incubation in 0.2% collagenase (type II, Sigma Chemical Co., St. Louis, Mo.) at room temperature, individual Dumont stage V and VI oocytes were transferred to an incubator and maintained overnight in Barth's solution (NaCl 84 mM, NaHCO$_3$ 2.4 mM, MgSO$_4$ 0.82 mM, KCl 1 mM, Ca(NO$_3$)$_2$ 0.33 mM, CaCl$_2$ 0.41 mM, Tris/HCl 7.5 mM, pyruvate 2.5 mM, gentamycin 50 μg/mL, penicillin-streptomycin, 100 units/mL, pH 7.4) at 18-20° C. and used for experiments 1-5 days post-injection. Oocytes were injected solution using an electronic microinjector (Drummond, Broomall, Pa.) with 50 mL of RNA containing 0.3-0.5 ng of each subunit RNA in a 1:1:1 ratio. The injected oocytes were used for experiments after 1-5 days of incubation in Barth's solution at 18-20° C.

Electrophysiology

Measurements of ion currents from oocytes expressing GABA$_A$ receptors were performed using a Warner two-electrode voltage-clamp amplifier (Warner Instruments, Inc., Foster City, Calif.) (Park-Chung, M., et al. (1999) *Brain Res.* 830: 72-87 incorporated herein in its entirety). Microelectrodes were fabricated from borosilicate glass capillaries with a programmed pipette puller (Sutter Instrument Co., CA). Microelectrode resistance was 1-3 MΩ when filled with 3 M KCl. The oocyte recording chamber was continuously perfused with Ringer solution. Oocytes were clamped at a holding potential of −70 mV during data acquisition. The membrane current was filtered at 10 Hz and sampled at 100 Hz. Compounds were applied by a gravity-driven external perfusion system. The working volume of the recording chamber was 30 μL and the rate of the perfusion was approximately 50 μL/sec. Compound application was 10-20 sec followed by a 90 sec wash. Data acquisition and external perfusion was computer controlled by custom-developed software. All experiments were performed at room temperature (22-24° C.). Dose-response data from each oocyte were fitted to the Hill equation by non-linear regression using the equation:

$$I_{GABA} = Emax/(1+(EC_{50}/c)^{nH})$$

Emax is the maximum response, EC$_{50}$ is the concentration producing 50% of the maximal response, n$_H$ is the Hill coefficient and c is the concentration of agonist. Based on the GABA concentration-response curve fit, an EC$_{10}$ for GABA was determined for each subunit combination, and this concentration was used for subsequent modulator concentration-response studies. Peak current measurements were normalized and expressed as a fraction of the peak control current measurements. Control current responses to an EC$_{10}$ concentration of GABA were re-determined after every 2-4 modulator applications. Percent modulation was determined by the equation:

$$\% \text{ change} = (I'/I-1) \times 100$$

where I is the control response at the GABA EC$_{10}$ and I' the response in the presence of modulator (Lippa A, et al. (2005) *Proc. Natl. Acad. Sci. USA* 102(20): 7380-7385 incorporated herein in its entirety).

Some compounds showed positive modulation and some showed negative modulation at a screening concentration of 10 μM.

Object Recognition Assay

Effect on animal behavior, specifically improvement of cognitive function (including but not limited to both short-term/working memory and long-term memory), can be determined using a number of established protocols. One method, novel object recognition, is described below.

Object Recognition Assay

Object recognition is an ethologically relevant task for rodents, which does not result from negative reinforcement (foot shock). This task relies on the natural curiosity of rodents to explore novel objects in their environments more than familiar ones. Obviously, for an object to be "familiar," the animal must have attended to it before and remembered that experience. Hence, animals with better memory will attend and explore a new object more than an object familiar to them. During testing, the animal is presented with the training object and a second, novel one. Memory of the training object renders it familiar to the animal, and it then spends more time exploring the new novel object rather than the familiar one (Bourtchouladze, R., et al. (2003) *Proc. Natl. Acad. Sci. USA* 100: 10518-10522 incorporated herein in its entirety). Recent neuroimaging studies in humans demonstrated that memory in object recognition depends on prefrontal cortex (PFC) (Deibert, E., et al. (1999) *Neurology* 52: 1413-1417 incorporated herein in its entirety). Consistent with these findings, rats with the PFC lesions show poor working memory when they are required to discriminate between familiar and novel objects (Mitchell, J. B. and Laiacona, J. (1998) *Behav. Brain Res.* 97: 107-113 incorporated herein in its entirety). Other studies on monkeys and rodents suggest that the hippocampus is important for novel object recognition (Teng, E. et al. (2000) *J. Neuroscience* 20: 3853-3863 incorporated herein in its entirety; Mumby, D. G. (2001) *Behavioural Brain Research* 127: 159-181 incorporated herein in its entirety). Hence, object recognition provides an excellent behavioral model to evaluate drug-compound effects on cognitive task associated with function of hippocampus and cortex.

The strength of memory retention in most cases is dependent on the amount of training (repetition of explicit or implicit trials). This "memory acquisition curve" can be influenced by many experimental and physical variables, which include, but are not limited to, temperature, humidity, ambient noise, lighting levels, the size of the training arena, the size and dimensions of the objects, the physical textures and colors of the training arena and the animal's stress levels, motivational states or experiences prior to training. To evaluate memory enhancing compounds for NOR, the experimenter must parameterize training duration to define (i) the duration (amount of training) required to reach an asymptotic (high) level of memory retention and (ii) a lesser duration at which memory retention is sub-maximal. Memory enhancing compounds will produce higher memory retention with sub-maximal training (but may have no measurable effect with asymptotic ("maximal") training). Typically, the difference between sub-maximal and asymptotic memory must be sufficiently larger to yield appropriate statistical power. An example which follows:

Prior to initiation of training, animals were handled and habituated to the training arena. Appropriately sized arenas were used for different species (e.g. for mice: a Plexiglas box of L=48 cm; W=38 cm and H=20 cm; for rats: a Plexiglas box of L=70 cm; W=60 cm and H=35 cm). The day before training, an individual animal was placed into a training apparatus located in a dimly lit room and allowed to habituate to the environment for 15 minutes (also see (Pittenger, C., et al. (2002) *Neuron* 34: 447-462 incorporated herein in its entirety; Bourtchouladze, R., et al. (2003) *Proc. Natl. Acad. Sci. USA* 100: 10518-10522 incorporated herein in its entirety). Training was initiated 24 h hours after habituation. An animal was placed back into the training box, which contained two identical objects (e.g. a small conus-shape object), and was allowed to explore these objects. The objects were placed into the central area of the box and the spatial position of objects (left-right sides) was counterbalanced between subjects. Animals were trained for 15 minutes. To test for memory retention, animals were observed for 10 minutes 24 hours after training. A rodent was presented with two objects, one of which was used during training, and thus was 'familiar' and the other of which was novel (e.g. a small pyramid-shape object). To ensure that the discrimination targets do not differ in smell, after each experimental subject, the apparatus and the objects were thoroughly cleaned with 90% ethanol, dried and ventilated for a few minutes.

The experiments were videotaped via an overhead video camera system. Types were then reviewed by a blinded observer and the following behavioral parameters were determined: time of exploration of an each object; the total time of exploration of the objects; number of approaches to the objects; and time (latency) to first approach to an object. The discrimination index—memory score—was determined as described previously (Ennaceur, A. and Aggleton, J. P. (1997) *Behav. Brain Res.* 88: 181-193 incorporated herein in its entirety; Bourtchouladze, R., et. al. (2003) *Proc. Natl. Acad. Sci. USA* 100: 10518-10522 incorporated herein in its entirety). This Data was analyzed by Student's unpaired t test using a software package (Statview 5.0.1; SAS Institute, Inc). All values in the text and figures are expressed as mean±SEM.

For NOR, 1-hr memory retention represents a measure of decremental, short-term memory (usually transcription independent), which contributes to cognitive functions, such as working memory (radial arm maze, delayed match to sample, etc), executive function (task-switching, etc.) and attentional processes (priming, etc). Twenty-four hour memory retention represents a measure of long-term memory, to which STM is converted through the molecular and cellular processes of memory consolidation. LTM contributes to lasting cognitive functions such as reference memory.

It will be appreciated by those skilled in the art that changes could be made to the embodiments described above without departing from the broad inventive concept thereof. It is understood, therefore, that this invention is not limited to the particular embodiments disclosed, but it is intended to cover modifications that are within the spirit and scope of the invention, as defined by the appended claims.

What is claimed:
1. A method of treating an animal in need of enhancement of memory or cognition comprising administering to the animal an effective amount of a compound of formula (I):

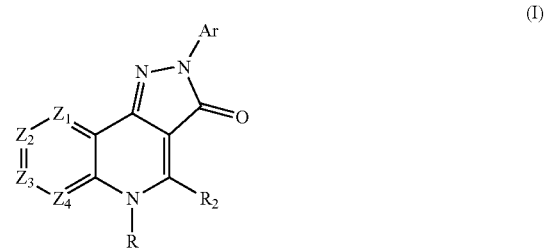

or tautomer thereof, or their pharmaceutically acceptable salts,
wherein:
R is hydrogen, or oxide;
$Z_1$, $Z_2$, $Z_3$, and $Z_4$ are each independently N, or $C(R_1)$, wherein at least one of $Z_1$, $Z_2$, $Z_3$, or $Z_4$ are N and at least two of $Z_1$, $Z_2$, $Z_3$, or $Z_4$ are $C(R_1)$;
each $R_1$ is independently selected from the group consisting of hydrogen, hydroxy, halo, cyano, $B^1$, —CON$R_aR_b$, hydroxy($C_1$-$C_6$)alkyl, aryl, heteroaryl, heterocycle, amino($C_1$-$C_6$)alkyl, ($C_1$-$C_6$)alkyl optionally substituted with up to 5 fluoro, and ($C_1$-$C_6$)alkoxy optionally substituted with up to 5 fluoro, wherein at least one $R_1$ is $B^1$;
$B^1$ is

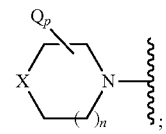

$R_2$ is selected from the group consisting of hydrogen, hydroxy, halo, hydroxy($C_1$-$C_6$)alkyl, ($C_1$-$C_6$)alkyl optionally substituted with up to 5 fluoro, and ($C_1$-$C_6$) alkoxy optionally substituted with up to 5 fluoro;
each $R_a$ and $R_b$ is independently hydrogen, ($C_1$-$C_6$)alkyl, aryl, heteroaryl, heterocycle, ($C_1$-$C_6$)alkylaryl, —S(O)$_z$($C_1$-$C_6$)alkyl, —S(O)$_z$aryl, —C(O)($C_1$-$C_6$)alkyl, —C(O)NR$_g$($C_1$-$C_6$)alkyl, —C(O)NR$_g$aryl, —C(O)O($C_1$-$C_6$)alkyl, arylOC(O)— or arylC(O)—, or $R_a$ and $R_b$ are taken together with the nitrogen to which they are attached to form a heterocycle group optionally substituted with one or more $R_d$; wherein the heterocycle group optionally comprise one or more groups selected from the group consisting of O (oxygen), S (sulfur), and NR$_c$;
each $R_c$ is independently hydrogen, ($C_2$-$C_6$)alkenyl, ($C_2$-$C_6$)alkynyl, —C(O)O($C_1$-$C_6$)alkyl, —C(O)Oaryl, ($C_1$-$C_6$)alkoxy($C_1$-$C_6$)alkyl, hydroxy($C_1$-$C_6$)alkyl, aryl, heteroaryl, heterocycle, arylO($C_1$-$C_6$)alkyl, —C(O)NR$_g$ ($C_1$-$C_6$)alkyl, —C(O)NR$_g$aryl, —S(O)$_z$($C_1$-$C_6$)alkyl, —S(O)$_z$aryl, —C(O)($C_1$-$C_6$)alkyl, arylC(O)—, ($C_1$-$C_6$) alkyl optionally substituted with up to 5 fluoro, or ($C_1$-$C_6$)alkoxy optionally substituted with up to 5 fluoro;
each $R_d$ is independently hydrogen, halo, oxo, hydroxy, —C(O)NR$_e$R$_f$, —NR$_e$R$_f$, hydroxy($C_1$-$C_6$)alkyl, aryl, aryl($C_1$-$C_6$)alkyl, ($C_1$-$C_6$)alkyl optionally substituted with up to 5 fluoro, or ($C_1$-$C_6$)alkoxy optionally substituted with up to 5 fluoro;

each $R_e$ and $R_f$ is independently selected from hydrogen, ($C_1$-$C_6$)alkyl, aryl, heteroaryl, heterocycle, ($C_1$-$C_6$) alkylaryl, aryl($C_1$-$C_6$)alkyl, —C(O)($C_1$-$C_6$)alkyl, —S(O)$_z$($C_1$-$C_6$)alkyl, —S(O)$_z$NR$_g$($C_1$-$C_6$)alkyl, —S(O)$_z$aryl, —C(O)NR$_g$($C_1$-$C_6$)alkyl, —C(O)($C_1$-$C_6$)alkyl, arylC(O)—, arylOC(O)—, or —C(O)O($C_1$-$C_6$)alkyl;

$R_g$ is hydrogen, aryl, heteroaryl, heterocycle, or ($C_1$-$C_6$)alkyl optionally substituted with up to 5 fluoro;

Ar is aryl optionally substituted with one or more M or heteroaryl optionally substituted with one or more M;

each Q is independently hydrogen, halo, oxo, hydroxy, —C(O)NR$_a$R$_b$, —NR$_a$R$_b$, ($C_1$-$C_6$)alkyl optionally substituted with up to 5 fluoro, ($C_1$-$C_6$)alkoxy optionally substituted with up to 5 fluoro, ($C_1$-$C_6$)alkyl optionally substituted with one or more R$_d$, hydroxy($C_1$-$C_6$)alkyl optionally substituted with one or more R$_d$, aryl optionally substituted with one or more R$_d$, or aryl($C_1$-$C_6$)alkyl optionally substituted with one or more R$_d$;

each M is independently hydrogen, halo, $CF_3$, $CF_2H$, hydroxy, cyano, nitro, ($C_1$-$C_6$)alkyl, hydroxy($C_1$-$C_6$)alkyl, ($C_1$-$C_6$)alkoxy, —NR$_a$R$_b$, aryl, heteroaryl or heterocycle;

each X is independently NL, oxygen, C(O)$_2$, or S(O)$_z$;

each L is independently hydrogen, ($C_2$-$C_6$)alkenyl, ($C_2$-$C_6$)alkynyl, —C(O)O($C_1$-$C_6$)alkyl, —C(O)Oaryl, ($C_1$-$C_6$)alkoxy($C_1$-$C_6$)alkyl, hydroxy($C_1$-$C_6$)alkyl, aryl, heteroaryl, heterocycle, arylO($C_1$-$C_6$)alkyl, —CONR$_e$R$_f$, —S(O)$_z$($C_1$-$C_6$)alkyl, —S(O)$_z$aryl, —C(O)($C_1$-$C_6$)alkyl, arylC(O)—, —C(O)NR$_g$($C_1$-$C_6$)alkyl, ($C_1$-$C_6$)alkyl optionally substituted with up to 5 fluoro, or ($C_1$-$C_6$)alkoxy optionally substituted with up to 5 fluoro;

p is an integer selected from 0, 1, 2 and 3;

z is an integer selected from 0, 1 and 2; and n is an integer selected from 0, 1, and 2.

2. The method of claim 1, wherein:

each $R_1$ is independently selected from the group consisting of hydrogen, hydroxy, halo, cyano, $B^1$, —CONR$_a$R$_b$, —NR$_a$R$_b$, hydroxy($C_1$-$C_6$)alkyl, amino($C_1$-$C_6$)alkyl, ($C_1$-$C_6$)alkyl optionally substituted with up to 5 fluoro, and ($C_1$-$C_6$)alkoxy optionally substituted with up to 5 fluoro, wherein at least one $R_1$ is $B^1$;

each $R_a$ and $R_b$ is independently hydrogen, ($C_1$-$C_6$)alkyl, —S(O)$_z$($C_1$-$C_6$)alkyl, —C(O)($C_1$-$C_6$)alkyl, —C(O)NR$_g$($C_1$-$C_6$)alkyl, or —C(O)O($C_1$-$C_6$)alkyl, or R$_a$ and R$_b$ are taken together with the nitrogen to which they are attached to form a heterocycle group optionally substituted with one or more R$_d$; wherein the heterocycle group optionally comprise one or more groups selected from the group consisting of O (oxygen), S (sulfur), and NR$_c$;

each $R_c$ is independently hydrogen, ($C_2$-$C_6$)alkenyl, ($C_2$-$C_6$)alkynyl, —C(O)O($C_1$-$C_6$)alkyl, ($C_1$-$C_6$)alkoxy($C_1$-$C_6$)alkyl, hydroxy($C_1$-$C_6$)alkyl, —C(O)NR$_g$($C_1$-$C_6$)alkyl, —S(O)$_z$($C_1$-$C_6$)alkyl, —C(O)($C_1$-$C_6$)alkyl, ($C_1$-$C_6$)alkyl optionally substituted with up to 5 fluoro, or ($C_1$-$C_6$)alkoxy optionally substituted with up to 5 fluoro;

each $R_d$ is independently hydrogen, halo, oxo, hydroxy, —C(O)NR$_e$R$_f$, —NR$_e$R$_f$, hydroxy($C_1$-$C_6$)alkyl, ($C_1$-$C_6$)alkyl optionally substituted with up to 5 fluoro, or ($C_1$-$C_6$)alkoxy optionally substituted with up to 5 fluoro;

each $R_e$ and $R_f$ is independently selected from hydrogen, ($C_1$-$C_6$)alkyl, —C(O)($C_1$-$C_6$)alkyl, —S(O)$_z$($C_1$-$C_6$)alkyl, —S(O)$_z$NR$_g$($C_1$-$C_6$)alkyl, —C(O)NR$_g$($C_1$-$C_6$)alkyl, —C(O)($C_1$-$C_6$)alkyl, or —C(O)O($C_1$-$C_6$)alkyl;

each Q is independently hydrogen, halo, oxo, hydroxy, —C(O)NR$_a$R$_b$, —NR$_a$R$_b$, ($C_1$-$C_6$)alkyl optionally substituted with up to 5 fluoro, ($C_1$-$C_6$)alkoxy optionally substituted with up to 5 fluoro, ($C_1$-$C_6$)alkyl optionally substituted with one or more R$_d$, hydroxy($C_1$-$C_6$)alkyl optionally substituted with one or more R$_d$, or aryl($C_1$-$C_6$)alkyl optionally substituted with one or more R$_d$;

each M is independently hydrogen, halo, $CF_3$, $CF_2H$, hydroxy, cyano, nitro, ($C_1$-$C_6$)alkyl, hydroxy($C_1$-$C_6$)alkyl, ($C_1$-$C_6$)alkoxy, or —NR$_a$R$_b$; and each L is independently hydrogen, ($C_2$-$C_6$)alkenyl, ($C_2$-$C_6$)alkynyl, —C(O)O($C_1$-$C_6$)alkyl, ($C_1$-$C_6$)alkoxy($C_1$-$C_6$)alkyl, hydroxy($C_1$-$C_6$)alkyl, aryl, heteroaryl, heterocycle, —CONR$_e$R$_f$, —S(O)$_z$($C_1$-$C_6$)alkyl, —C(O)($C_1$-$C_6$)alkyl, arylC(O)—, —C(O)NR$_g$($C_1$-$C_6$)alkyl, ($C_1$-$C_6$)alkyl optionally substituted with up to 5 fluoro, or ($C_1$-$C_6$)alkoxy optionally substituted with up to 5 fluoro.

3. The method of claim 1 wherein said animal has an anxiety disorder, sleep disorder, depression, or schizophrenia.

4. The method of claim 3 wherein said animal has Parkinson's disease, or Huntington's disease.

5. The method of claim 1, wherein said animal has head trauma.

6. The method of claim 1 wherein the animal is an aged animal.

7. The method of claim 1 wherein said animal has Alzheimer's disease.

* * * * *

UNITED STATES PATENT AND TRADEMARK OFFICE
CERTIFICATE OF CORRECTION

Page 1 of 1

PATENT NO.          : 8,497,262 B2
APPLICATION NO.     : 12/949619
DATED               : July 30, 2013
INVENTOR(S)         : Kaplan et al.

It is certified that error appears in the above-identified patent and that said Letters Patent is hereby corrected as shown below:

In the Specification

Column 4, Line 29, please delete "hetero aryl" and insert therefore, --heteroaryl--.

Column 4, Line 30, please delete "C(O)$_2$," and insert therefore, --C(Q)$_2$,--.

Column 21, Line 62, please delete "C(O)$_2$," and insert therefore, --C(Q)$_2$,--.

Column 23, Line 12, directly below "DETAILED DESCRIPTION OF THE INVENTION" please insert:

--As used herein, common organic abbreviations are defined as follows:--.

Column 23, Line 48, please delete "isopropy," and insert therefore, --isopropyl,--.

Column 25, Line 36, please delete "scope" and insert therefore, --scope.--.

Column 39, Line 41, please delete "piperazin" and insert therefore, --Piperazin--.

Column 41, Line 35, please delete "carboxyate" and insert therefore, --carboxylate--.

Column 43, Line 3, please delete "carboxyate" and insert therefore, --carboxylate--.

Column 55, Line 27, please delete "50 mL" and insert therefore, --50 nL--.

In the Claims

Column 58, Line 28, after "—CONR$_a$R$_b$," please insert -- —NR$_a$R$_b$,--.

Column 59, Line 27, please delete "C(O)$_2$," and insert therefore, --C(Q)$_2$,--.

Signed and Sealed this
Eleventh Day of March, 2014

Michelle K. Lee
*Deputy Director of the United States Patent and Trademark Office*